(12) United States Patent
Lin

(10) Patent No.: US 8,722,613 B2
(45) Date of Patent: May 13, 2014

(54) METHODS AND COMPOSITIONS FOR INHIBITION OF NUCLEAR FACTOR KAPPAB

(75) Inventor: Li Lin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1066 days.

(21) Appl. No.: 10/569,884

(22) PCT Filed: Aug. 27, 2004

(86) PCT No.: PCT/US2004/027923
§ 371 (c)(1),
(2), (4) Date: Sep. 29, 2008

(87) PCT Pub. No.: WO2005/021722
PCT Pub. Date: Mar. 10, 2005

(65) Prior Publication Data
US 2009/0099107 A1    Apr. 16, 2009

Related U.S. Application Data

(60) Provisional application No. 60/499,195, filed on Aug. 29, 2003.

(51) Int. Cl.
*A61K 31/00* (2006.01)
*A61K 39/395* (2006.01)

(52) U.S. Cl.
USPC ........................................ 514/1.1; 424/130.1

(58) Field of Classification Search
None
See application file for complete search history.

(56) References Cited

U.S. PATENT DOCUMENTS 5,324,818 A    6/1994    Nabel et al.
2002/0068690 A1    6/2002    Baldwin et al.

OTHER PUBLICATIONS

Bhakar et al., Constitutive Nuclear Factor-kB Activity is Required for Central Neuron Survival; The Journal of Neuroscience, Oct. 2002, vol. 22, pp. 8466-8475.*
Pajonk et al., Inhibition of NF-kB, Clonogenicity, and Radiosensitivity of Human Cancer Cells; JNCI J Natl Cancer Inst, 1999, vol. 91, pp. 1956-1960.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Liou et al., The NF-kappa B p50 precursor, p105, contains an internal I kappa B-like inhibitor that preferentially inhibits p50, EMBO J. (1992), vol. 11(8), pp. 3003-3009.*

* cited by examiner

*Primary Examiner* — Alexander Kim
(74) *Attorney, Agent, or Firm* — Edwards Wildman Palmer LLP; Peter F. Corless

(57) ABSTRACT

A series of p105-based NF-κB super repressors, designated p-105(sr), have been designed. The p105(sr), no longer generates p50 and undergoes signal-induced degradation, effectively inhibiting all NF-κB activities. Additionally, p105(sr) significantly enhances tumor necrosis factor alpha (TNF-α)-mediated killing of MT1/2 skin papilloma cells when p50 homodimer activity is elevated. p105(sr) is an effective NF-κB super repressor with a broader range than other currently available IkBα super repressors. The novel repressor can be used in cells where a noncanical NF-κB activity is dominant or multiple NF-κB activities are activated.

4 Claims, 8 Drawing Sheets

METHODS AND COMPOSITIONS FOR INHIBITION OF NUCLEAR FACTOR KAPPAB

RELATED APPLICATIONS

This application is the U.S. national phase application, pursuant to 35 U.S.C. §371, of PCT International Application Ser. No. PCT/US04/27923, filed Aug. 27, 2004, designating the United States and published in English, claims priority to U.S. Provisional Application Ser. No. 60/499,195, filed Aug. 29, 2003, the entire contents of which are incorporated herein by reference.

This invention was supported in part by a grant no. CA98252 from the National Institutes of Health. The United States Government has rights in the invention.

BACKGROUND OF THE INVENTION

1. Field of the Invention

The present invention relates to the field of medical arts; more particularly to broad range inhibitors of nuclear factor kB (NF-kB) and the use of these inhibitors in cancer therapy and in treating inflammatory diseases.

2. Background

Nuclear Factor-kB (NF-kB)

NF-kB is a transcription factor controlling a variety of biological responses. It appears to be involved in several human diseases, including, among others, cancer, stroke, diabetes and AIDS. NF-kB is composed of a family of related proteins with a conserved central region, which is known as the Rel homology domain. This region is involved in DNA binding, interactions with IkB (inhibitor molecules) and dimerization. The five related-family members in mammals include p50/p105, p65/RelA, cRel, RelB and p52/p100. There are multiple dimeric forms of NF-kB which form homo and heterodimers, with some forms more dominant than others.

There are several forms of NF-kB inhibitor, IkB. IkBs inhibit NF-kB formation by retaining these dimers in the cytoplasm or preventing them from binding to the kB element, not by inhibiting formation of the dimeric form of NF-kB. Typical IkBs tend to bind specific NF-kB species. IkBα for example exhibits homology with the COOH terminus of the p105 of NF-kB, while IkBβ and IkBε interact with similar subunits. Each inhibitor tends to control specific kB species, so that none of the currently known IkB inhibitors prevents NF-kB interaction with all NF-kB species.

NF-kB is rapidly activated in the cell by stimuli such as inflammatory cytokines, including TNF-α, IL-1, T-cell activation signals, growth factors and stress inducers. Once activated, NF-kB binds to target DNA elements in the nucleus causing positive regulation of gene transcription involved in immune and inflammatory responses, cell growth and, importantly, apoptosis. Among the genes regulated by NF-kB are the interleukins such as IL-2, IL-6, IL-8, IL-2 receptor, IL-12 p40 subunit, VCAM-1, ICAM-1, TNF-α, IFN-γ and cMyc.

Apoptosis is of particular interest because once activated, NF-kB inhibits apoptosis. Under normal conditions, NF-kB activation is transient because of mechanism within the cell that cause its deactivation. Oncoproteins have been demonstrated to activate NF-kB, which by inhibiting apoptosis allow cell proliferation. Thus there is the desirability of preventing the action of NF-kB in treating malignancies, particularly when anti-cancer drugs intended to promote apoptosis are administered.

Additionally, NF-kB is thought to be a primary effector in a number of human diseases. The molecule is the subject of current research aimed at understanding its action and to apply this knowledge to the development of agents that can be used alone or in conjunction with anticancer and anti-inflammatory drugs.

Deficiencies in the Art

There is a recognized need to identify compositions that inhibit NF-kB activity, particularly due to its role in inflammation and apoptosis. Several NF-kB inhibitors have been prepared, but none is effective against all NF-kB species. There is therefore a need for a broader "super repressor" NF-kB inhibitor that interacts with p50 and p52 as well as RelB and would be an effective adjuvant in cancer and anti-inflammatory therapy.

SUMMARY OF THE INVENTION

The present invention addresses several problems with current methods that attempt to control NF-kB activation. In particular, a p105 "super repressor" is disclosed, which represses not only TNF-α induced NF-kB (p50/RelA) activity but also NF-kB p105 homodimer activity. The homodimer cannot be repressed by currently available inhibitors of NF-kB, specifically IkBα(sr). The novel p105(sr) proteins can be employed in cancer therapies that involve chemotherapy and/or radiation and will act to inhibit the anti-apoptosis effects caused by activation of NF-kB induced by these therapies. These treatment methods typically promote apoptosis but this process is inhibited because of concurrent stimulation of NF-kB. The novel p105 super repressors can be employed in conjunction with treatment of various chronic and acute diseases that activate NF-kB, including many inflammatory diseases.

p105(sr) is an unexpectedly improved super repressor compared with NF-kB repressors based on IkBα, which are currently widely used in research and experimental therapeutics. However, since IkBα interacts with only two NF-kB species, RelA and c-Rel, its introduction into cells does not generate a true NF-LB null phenotype in TNFα-mediated apoptosis tests in skin cancer/tumor cell lines. In contrast, p105(sr) has the advantage of interacting with all NF-kB species with strong affinity, and hence is a broader range super repressor. As shown in TNFα-mediated apoptosis tests in several cell lines, p105(sr) is more effective in enhancing apoptosis than IkBα.

Several new super repressors were generated by modification of wildtype p105. NF-kB transcription factor p50 and the Rel protein-specific inhibitor are encoded by a nfkb gene, (SEQ ID NO. 1 and SEQ ID NO. 3, the corresponding polypeptides of which are set forth in SEQ ID NO. 2 and SEQ ID NO: 4, respectively). Generation of p50 requires the proteasome activities. Similar to IkBs, p105 is also degraded via the proteasome when the cell is stimulated, releasing the bound NF-kB species into the nucleus. To generate a super repressor, one needs to abolish p50 biogenesis; i.e., to make the gene not contribute more transcription factor, and make p105 not undergo immediate degradation upon stimulation; i.e., not release the bound NF-kB into the nucleus. The p105 mutants, p105(sr), satisfy these requirements. It has been demonstrated that p105(sr) and related super repressors maintain the ability to interact with five NF species, p50, p52, RelA, RelB and c-Rel, and effectively repress NF-kB activities. Furthermore, p105(sr) greatly enhances TNFα-mediated apoptosis.

An important aspect of the invention is the p105(sr) mutant polypeptide encoded by a modified nfkb1 gene (SEQ ID NO. 5) having deletions in the midregion and at the C-terminus. It is believed that one may delete relatively large segments from this region yet retain the desirable inhibitory properties of the encoded polypeptide; i.e., from 50 to about 200 nucleotides from the mid region and/or the C-terminus. In certain embodiments, the p105(sr) encoding gene contains deletions in the mid region but preserves a nuclear localization signal (SEQ ID NO. 7). In a preferred embodiment, the entire contiguous segments of the nfkb1 gene between positions 356 and 498 and between positions 800-971 are deleted (SEQ ID NO.5) such that a p105 super repressor having the amino acid sequence of SEQ ID NO. 6 is expressed.

The middle region of the nfkb gene can be further modified by maintaining the native nuclear localization signal (NLS). A p105(sr) that retains the NLS has inhibitory activity as the p105(sr) having SEQ ID NO. 5. It is clear that selected deletions, taking care that the deletions do not affect DNA binding and dimerization with all, rather than just the Rel-containing species of NF-kB. Moreover, it is believed that preserving the nuclear localization signal (NLS) in the C-terminal region, such as in SEQ ID NO. 7, is believed to allow the expressed p105(sr) to enter the nucleus and exert its inhibitory function. All p105(sr) repressors encoded by the modified genes containing the NLS have similar inhibitory efficiency.

In certain applications, it may be desirable to prolong the in vivo half-life of the repressors. It is believed that selected mutations at the C-terminal phosphorylation targets in the nfkb gene may have this effect.

Modifications to the p105(sr) that provide an effective broad range super repressor should take into account that all functional elements except that required for processing (the middle region) and degradation (the C-terminal region) signals remain intact. Rhe Rel homology domain (RHD) at the N-terminal regions is required for DNA binding and dimerization with other NF-kB species. The C-terminal ankaryn repeats should also remain intact as this regions also interacts with the RHD and keeps the protein the cytoplasm.

The invention also embodies related polypeptides that are readily prepared and tested for NF-kB repressor activity. Any number of nucleotides may be deleted from the midsection of the nkfb gene or homologous genes, including nfkb1 and nfkb2 genes. The human nfkb gene is over 90% identical to the mouse gene and can be modified in the same manner as the mouse gene used as a model. Thus, it is a matter of routine procedure to delete a single nucleotide or up to the entire p105 coding region and to test the encoded polypeptides for NF-kB inhibition. There are two signal sequences in the p105 coding region, making it necessary when selecting additional p105 (sr) inhibitors to determine whether or not these regions must be deleted in order to obtain an effective inhibitor. Accordingly, the present invention includes the family of p105 based super repressors that can be obtained from a wide range of deletions in the mid and C-terminus regions of a nfkb gene, preferably any number of deletions up to about 142 nucleotides in the mid region and up to 171 nucleotides at the 3' end. Thus, 5-10, 20-25, 50-60, 65-75 nucleotides and so forth are contemplated deletions.

It is believed that, while at least in nfkb1 the C-terminus deletions are required in order to prevent degradation, a somewhat fewer number of deletions may not adversely affect the activity of the expressed polypeptide. In the case of p100, the C-terminal deletion may not be required.

The invention also includes related polypeptides that are at least 60%, preferably 70-75%, more preferable 80-90% and most preferably at least 90% identical to the described p105 (sr) and can be readily identified by homology searches conducted in standard data bases.

In an important aspect of the invention, intervention in controlling malignancies and diseases associated with inflammation can be achieved using the p-105 based super repressors disclosed herein. In general, one administers appropriate pharmaceutically acceptable compositions to subjects having these disease conditions in an amount deemed sufficient to inhibit NF-kB binding to any of its normal or atypical dimeric partners. The compositions are formulated in pharmaceutically accepted vehicles. Alternatively, the DNA encoding the mutant p105(sr) polypeptides may be administered to the cell using any of several well-known methods of cell transformation. The pharmaceutical composition of claim 37 wherein the adjuvant is polyphosphazene, aluminum phosphate gel, algal glucan, gamma inulin/alum, aluminum hydroxide gel, calcitriol, calcium phosphate gel, cholera toxin B subunit, block copolymers, cytokine-containing liposomes, dehydroepiandrosterone, Frend's adjuvant, Il-1β, IL-2, IL-7, IL-12, *E. coli* enterotoxin, Pleuran, Pluronic L121, or protein cochleates.

The compositions may farther include an anti-inflammatory agent. Examples of such agents include Dalfon, Diflunisal, dolobid, fenoprofen, meclomen, porstel, tolectin, accolate, singulari, zyflo, advair, aerobid, azmacort flovent, pulmicoar, qvar, intal, tilade, prednisone, prednisolone or methyl prednosolone.

The compositions of the invention may also include the polypeptides encoded by the novel nucleic acids. The NF-kB inhibitor polypeptides are defined herein as "mutant p105" proteins or p105(sr), indicating the super repressor activity of these proteins. It should be recognized that the p105(sr) compositions may also include any of a number of appropriate therapeutic drugs required to treat a disease, such as malignant diseases and a wide range of inflammatory diseases.

Pharmaceutically acceptable compositions of the present invention are suitable for treatment of cancers or inflammatory diseases. Cancers include ofmelanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, leukemias and lymphomas. 31. Use of claim 29 wherein the inflammatory condition is selected from the group consisting of atherosclerosis, stroke, heart disease, asthma, and septic shock. Use of claim 29 wherein the inflammatory condition is selected from the group consisting of atherosclerosis, stroke, heart disease, asthma, and septic shock.

Inflammatory conditions may include atherosclerosis, stroke, heart disease, asthma, and septic shock Pharmaceutical Compositions Pharmaceutical compositions containing the form in which the p105(sr) is to be provided are preferably administered parenterally, intraperitoneally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin. Therapeutic compositions are contemplated for use with the disclosed constructs. Such compositions include comprise pharmaceutically acceptable carriers. Carrier refers to any substance suitable as a vehicle for delivering a nucleic acid molecule of the present invention. As used herein, a "carrier" refers to any substance suitable as a vehicle for delivering $^a$ nucleic acid molecule of the present invention to a suitable in vivo or in vitro site. As such, carriers can act as a pharmaceutically acceptable excipient of therapeutic compositions containing a nucleic acid molecule of the present invention. Preferred carriers are capable of entering the cell and being expressed by the cell. Carriers may include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers).

Examples of non-targeting carriers include, but are not limited to water, phosphate buffered saline, Ringer's solution, dextrose solution, serum containing solutions, Hank's solution, aqueous physiologically balanced solutions, oils, esters and glycols. Aqueous carriers may contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, phosphate buffers, Tris buffers, and bicarbonate buffers. Auxiliary substances may also include preservatives, such as thimerosal, m- and o-cresol, formalin and benzyl alcohol. Preferred auxiliary substances for aerosol delivery include surfactant substances non-toxic to an animal; for example, esters or partial esters of fatty acids containing from about six to about twenty-two carbon atoms. Examples include; caproic, octanoic, lauric, palmitic, stearic, linoleic, linolenic, olesteric, and oleic acids. Other carriers may include metal particles (e.g., gold particles) for use with, for example, a biolistic gun through the skin. Therapeutic compositions of the present invention may be sterilized by conventional methods and/or lyophilized.

Targeting carriers are referred to herein as "delivery vehicles." Delivery vehicles of the present invention are capable of delivering a therapeutic composition of the present invention to a target site in an animal. A "target site" refers to a site in an animal to which one desires to deliver a therapeutic composition. For example, a target site may be a malignant tumor cell, a non-malignant tumor cell, a lymph node or a lesion caused by an infectious agent, or an area around such cell, tumor or lesion, which is targeted by an infection or delivery using liposomes or other delivery vehicles.

Sterile injectable solutions are prepared by incorporating the active compounds in the required amount in the appropriate solvent with various of the other ingredients enumerated above, as required, followed by filtered sterilization Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Upon formulation, solutions will be administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Delivery of p105 Super Repressors to Cells

The nucleic acids encoding the mutant p105(sr) polypeptides obtained from the modified forms of nfb1 gene can be introduced into and expressed in a selected cell. Nucleic acids or naked DNA can be used to transform cells; however, in order to be effective it is believed that specific targeting modes may be desirable, such as the use of viral vectors, some of which are known to target specific cell types. Cell transformations can be accomplished using any of a variety of methods well-known in the art, such as targeted liposomes, viral and retroviral vectors, electroporation and direct injection with naked DNA. Viral vectors have been successfully used in in vivo applications. Adeno-associated virus, adeno virus, and herpes virus vectors can be modified to be non-replicative and have been successfully used for gene delivery. In vitro transformation may employ electroporation methods, which can also be used for ex vivo transformation procedures.

Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle may be modified to target a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting the vehicle to a preferred site, such as a specific organ or cell type.

Specific targeting causes a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the deli vehicle to a cancer cell. Tumor cell ligands include ligands capable of binding to a molecule on the surface of a tumor cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

A preferred delivery vehicle of the present invention is a liposome. A liposome is capable of remaining stable in an animal for a sufficient amount of time to deliver a nucleic acid molecule of the present invention to a preferred site in the animal. A liposome should be stable in the animal into which it has been administered for at least about 30 minutes, preferably for at least about 1 hour and even more preferably for at least about 24 hours.

A liposome may comprise a lipid composition that targets a nucleic acid molecule of the present invention to a particular, or selected, site in an animal. The lipid composition of the liposome may target to any organ of an animal, but preferably where cancer is involved to the cancer cells.

A liposome may include a lipid membrane of the targeted cell to deliver a nucleic acid molecule into a cell. The transfection efficiency of a liposome of the present invention should be at least about 0.5 microgram (pg) of DNA per 16 nanomole (nmol) of liposome delivered to about $10^6$ cells, more preferably at least about 1.0 μg of DNA per 16 nmol of liposome delivered to about $10^6$ cells, and even more preferably at least about 2.0 μg of DNA per 16 nmol of liposome delivered to about $10^6$ cells.

A preferred liposome size is between about 100 and about 500 nanometers (nm), more preferably between about 150 and about 450 nm and even more preferably between about 200 and about 400 nm in diameter.

Any liposome is believed to be suitable for use in delivering the nucleic acids of the present invention. Examples include liposomes conventionally used in gene delivery methods known to those of skill in the art. Particularly useful liposomes may include polycationic lipid compositions and/or liposomes having a cholesterol backbone conjugated to polyethylene glycol. One may also incorporate a tumor cell ligand exposed on the outer surface of the liposome, preferably a ligand from the particular tumor cells in a subject being treated for that type of cancer.

As a delivery vehicle, a liposome may be complexed with a nucleic acid molecule disclosed in the present invention. A suitable concentration of the nucleic acid molecule includes a concentration effective for delivering a sufficient amount of nucleic acid molecule to a cell such that sufficient polypeptide is expressed to regulate apoptosis by controlling NF-kB activity in a desired manner. Nucleic acid molecules may be combined with liposomes at a ratio of from about 0.1 μg to about 10 μg of nucleic acid molecule of the present invention per about 8 nmol liposomes, more preferably from about 0.5 μg to about 5 μg of nucleic acid molecule per about 8 nmol liposomes, and even more preferably about 1.0 μg of nucleic acid molecule per about 8 nmol/liposomes.

Other preferred delivery vehicles for nucleic acids comprise a recombinant virus particle. A recombinant virus particle includes at least a nucleic acid encoding one or more of the disclosed p105(sr) polypeptides operably in combination with a promoter that causes expression of the p105(sr) by the transformed cell. The recombinant molecules are packaged in a viral coat that allows entrance of DNA into a cell so that the DNA is expressed in the cell. A number of recombinant virus particles can be used, including, but not limited to, those based on adeno-associated virus, poxvirus, adenovirus, herpesvirus, baculovirus and retroviruses. For targeting of a specific cell, selected antibody may be incubated with the viral vector so that there is preferential infection of a particular cell.

In vivo delivery methods may employ intratumoral injection, intrathecal injection, transvascular delivery by intra-arterial or intravenous injection of vital particles carrying the modified nfkb gene. A wide range of viral delivery vectors is available and a choice will be made on considerations such as size of the DNA to be delivered and the targeting efficiency.

The nucleic acids encoding the NF-kB super repressors may be used to inhibit NF-kB transcriptional activity. One administers the nucleic acids, which are operable linked to an appropriate promoter, to a cell under such conditions as to allow expression of the super repressor to that transcriptional activity of NF-kB is inhibited. The super repressor will inhibit p50 dimer formation, and also inhibit B-cell activity and tumorgenesis.

The invention also includes a system for testing the efficiency of an expressed p105(sr) to inhibit formation of active NF-kB by determining the production of NF-kB in a selected cell when the cell is exposed to an agent that increases NF-kB levels in the cell. A selected cell is tranduced with a vector comprising a nucleic acid having the sequence of SEQ ID NO. 5 or SEQ ID NO. 7 operably linked to a promoter. Then the amount of NF-kB produced in non-transfected cells is compared with the amount produced after transduction of the cell. The efficiency of inhibition can then be calculated based on decrease in amount of NF-kB in the transduced cell. Exemplary selected cells include tumorigenic cells. Agents that increase NF-kB levels in the cell include inflammatory agents such as cytokines, particularly IL-2, IL-7, IL-12 and IL1β or combinations of inflammatory agents.

BRIEF DESCRIPTION OF THE DRAWINGS

FIG. 2A, co-transfection with p50.
FIG. 2B, co-transfection with p52.
FIG. 2C, co-transfection with RelA.
FIG. 2D, co-transfection with c-Rel.
FIG. 2E, co-transfection with RelB.

DETAILED DESCRIPTION OF THE INVENTION

Figure 1:
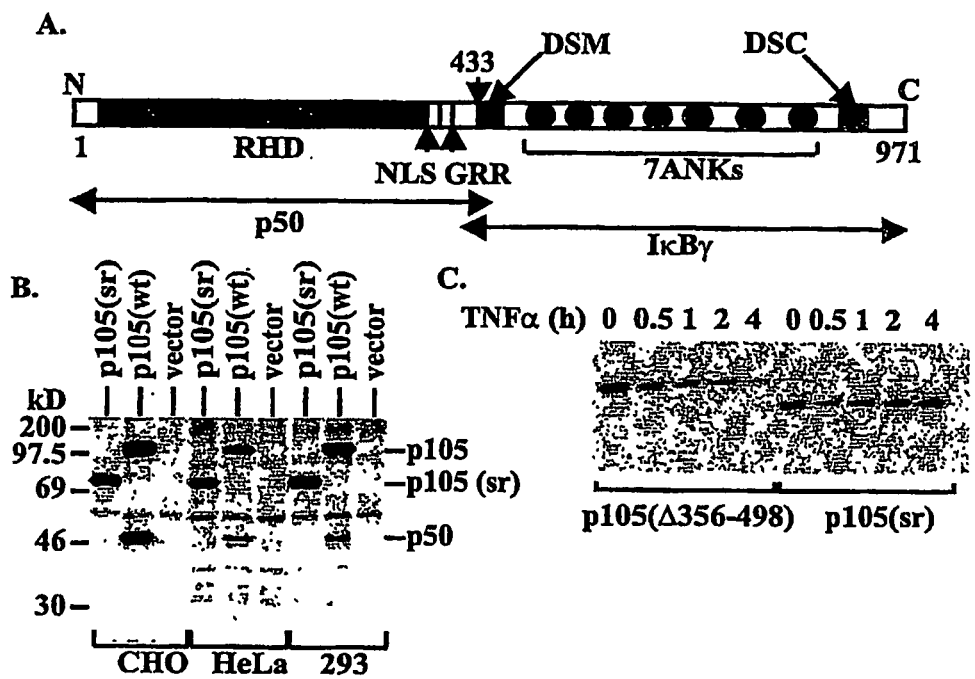
FIG. 1A. p105(sr) no longer generates p50 and does not respond to TNFa-induced degradation. A, anatomy of wild-type murine p105. Regions corresponding to p50 and IkBγ are shown, and residue 433 marks the C terminus of p50. GRR, the glycine-rich region; DSM, degradation signal in the middle of p105; DSC, degradation signal in the C terminus of p105 that includes the DD (SEQ ID NO. 5).
FIG. 1B shows that p105(sr) does not generate p50. gp10-tagged p105(sr) and p105(wt) were expressed in CHO-CD14, HeLa, and 293 cells. Twice the volume of HeLa cell lysates was loaded on the gel because expression in HeLa cells is lower. The lysates were resolved with SDS-PAGE (10%) and immunoblotted with anti-gp10 antibodies.
FIG. 1C shows that p105(sr) is stable upon TNFα treatment. p105(sr) is stable upon TNFα treatment. gp10-tagged p105(sr) and p105 (Δ365-498) were expressed in HeLa cells. The transfected cells were treated, labeled with [$^{35}$S]methionine/cysteine for 30 in, and chased with normal growth medium supplemented with TNFα (20 µg/ml) for the time indicated. At each time point, the cells were lysed and immunoprecipitated with anti-gp10 antibodies. The precipitants were then resolved with SDS-PAGE and visualized with fluorography.

The present invention relates to the design and generation of p105 super repressors that are repressors of NF-kB. The repressors are generated by deletion of residues 356-498 in the middle region of murine p105 and, preferably also by the C-terminal residues 800-971. These p105 deletion mutants no longer generate p50 or respond to stimuli to undergo degradation. The p105(sr) retains its ability to interact with at least five NF-kB species and inhibit tumor necrosis factor (TNF-α) induced NF-kB activities effectively. Unlike IkBα(sr), which does not interact with p50 and p52 and hence does not inhibit the homodimer activities, p105(sr) interacts with both proteins, and is shown to effectively inhibit p50 homodimer activity. In addition, p105(sr) is able to serve as a potent inhibitor for RelB, which is an important player in B-cell development.

Nuclear factor KB (NF-κB) is a latent dimeric complex sequestered in the cytoplasm by its inhibitor IkB. It is activated to engage transcription in the nucleus by various stimuli. Under normal physiological conditions such activation is transient, because of autoregulatory mechanisms. However, the NF-kB family of transcription factors is constitutively activated in many types of cancer cell and is thought to regulate anti-apoptosis factors that aid survival of the cancer cells.

The exemplary p105(sr) was generated from wild-type nfkb at 971-residue (2961 nucleotides). 14-residue were added to the N-terminus (12 are epitope tag residues, 2 are from the restriction site used to ligate the tag to the sequences. In the mid region, residues 356-498 were deleted, including the NLS, GRR and DSM. The GRR and DSM are required for generating p50. In the C-terminal region, residues 800-971 were deleted, which includes the DSC required for signal-induced degradation (see SEQ ID NO. 1). The original wild-type amino acid number is used. In the mid region to fill in 4 residues to link the N- and C-terminals and to keep the polypeptide in frame. At the C-terminus, 2 residues were added as the result of linker sequences. Therefore, p105(sr) has a new residue number that is different from the wildtype; for example, residue 1 is the T7gp10 tag residue. The translated p105(sr) polypeptide sequence is set forth in SEQ ID NO. 6, the total residues are 677 from 2034 nucleotides.

A further example of a p105(sr) is exemplified as SEQ ID NO. 8, encoded by a nucleic acid segment (SEQ ID NO. 7). The sequence is the same as SEQ ID NO. 5 except that the NLS is not deleted; i.e., the deletion is in the midregion from 365-498 of the nfkb gene. The total residues are 683 from 2052 nucleotides.

The p50 region of the murine nfkb gene is estimated as 433 residues of the N-terminal portion of the p105 component. The entire unprocessed protein includes p105 (971 residues). For the p105(sr), SEQ ID NO. 6, the p50 portion includes the first 356 residues or 370 if the 14 tag residue is added. For the p105(sr), represented by SEQ ID NO. 8, the first 365 residues plus 14 additional amino acids.

As indicated, NF-kB is a family of transcription factors that regulate immune and inflammatory responses, programmed cell death (apoptosis) and developmental processes. The active form of NF-kB is a dimer formed by two NF-kB proteins that bind to the kB sequences within the promoter. In normal cells, NF-kB is sequestered in the cytoplasm by its inhibitor IkBs. When the cell is stimulated, or, under pathological conditions such as inflammation, tumorigenesis and pathogen infections, IkBs are degraded through the proteasome pathway, and the released NF-kB complex translocates into the nucleus and activates genes that are controlled by the kB elements. One profound consequence of NF-kB activation is the expression of several anti-apoptotic cellular factors.

In cancer cells NF-kB is often found to be constitutively activated, and is thought to contribute to uncontrolled growth of the cancer cells. Persistent activation of NF-kB also contributes to chemoresistance of various cancers. Effective repression of NF-kB activity may curtail or relieve many pathological conditions and enhance drug or chemotherapy reagent-mediated cell killing.

Chemotherapy reagents induce death of cancer cells but also activate NF-kB pathways. Therefore, activation of NF-kB is a contributing factor of chemoresistance. Others have shown that an IkBα-based NF-kB super repressor (sr) introduced into cancer cells not only enhances stimuli-induced apoptosis but also facilitates systematic identification of genes regulated by NF-kB that may contribute to the malignancy and progression of the tumor.

Activation of prototypic NF-kB requires degradation of IkBs. The prerequisite of the process is stimuli-induced phosphorylation of IkBs by the IkB kinase-constituted signalsome. The NF-kB inhibitor, IkBα(sr), can be generated by either mutating serine 32 and 36, which are the targets of the IkB kinases or by deleting the N-terminal portion of IkBα that harbors these targets. IkBα (sr) suppresses stimuli-induced NF-kB activation, because the inhibitor now cannot be phosphorylated and therefore will not be subjected to immediate degradation, and the bound NF-kB subunits will not be released into the nucleus.

Although in most normal and cancer cells, the NF-kB activity detected is that of prototype p50/RelA heterodimer, atypical/noncanonical NF-kB species also play significant roles in gene regulations. For example, the RelB/p52 complex plays a key role in B cell development. It has also been observed that NF-kB p50 homodimer activity is significantly elevated in certain types of cancers such as murine B cell leukemia and chemical-promoted mouse skin carcinomas, and such elevation has been linked to the survival of the cancer cells. Furthermore, more than one species of NF-kB can be elevated in cancer cells, and broad inhibition of this family of proteins is pharmacologically and clinically significant.

Definitions

The following terms are defined to provide additional guidance to one of skill in the art in the practice of the invention.

The term "heterologous" when used with reference to portions of a nucleic acid, indicates that the nucleic acid comprises two or more subsequences which are not found in the same relationship in nature.

The terms "nucleic acid" and "polynucleotide" are used interchangeably, may refer to synthetic or non-naturally nucleic acids, or to deoxyribonucleotide or ribonucleotides in single or double-stranded form.

"Operably linked" refers to a functional relationship between two or more nucleic acid segments and generally refers to the functional relationship of a transcriptional regulatory sequence to a transcribed sequence.

"Sequence" of a gene or nucleic acid refers to the order of nucleotides in the polynucleotide, including either or both strands of a double-stranded DNA molecule.

"Identical" or "percent identity" refers to two or more sequences of a nucleic acid or polypeptide that are the same or have a specified percentage of nucleotides or amino acid residues that are the same, when aligned for maximum correspondence over a comparison length. The measurement may be made using well-known comparison algorithms, such as PILEUP, or by manual alignment and visual inspection. Thus nucleic acids within the scope of the invention include those with a nucleotide sequence identity that is at least about 60%, at least about 70%, at least about, 75% to about 85% and about 90% of the sequence of SEQ ID NO. 1. These levels of identity are understood to mean "substantially identical" within the bounds of the defined "percent identity".

NF-kB/rel Protein Inhibitors p105 is regarded as an atypical NF-KB/Rel protein inhibitor. It binds other Rel proteins and retains them in the cytoplasm. However, wild-type p105 cannot be employed as an NF-kB super repressor, because expression of the nfkb1 gene always produces both p105 and p50 in the cell, and the latter is a component of the NF-kB transcription complex. In addition, wild-type p105, like IkBα, also undergoes signal-induced complete degradation, releasing the bound NF-kB species into the nucleus.

Compared with IkBα, however, p105 possesses important features that make it potentially a broader range NF-kB super repressor. First, p105 interacts with all Rel proteins, including p50, p52, and RelB, with high affinity through the Rel homology domain (RHD) and IkBγ-like ankyrin repeats. Second, although both require the proteasome activity, p50 biogenesis and p105 degradation are separate processes. The middle region of p105, which contains a glycine-rich region and a putative degradation signal for the proteasome, is likely to be responsible for p50 generation. The C-terminus of p105, which harbors the consensus sequences for the IkB kinases, the ubiquitin ligase β-transducin repeat-containing protein, and a death domain (DD), is required for signal-induced p105 degradation. Because none of these cis-elements overlap with the RHD or IkBγ-like ankyrin repeats, mutations within these two areas may not interfere with the dimerization and inhibitory functions of the p105 protein. was pr Using this rationale, a novel mutant was designed with the aim of using this super repressor to inhibit cellular anti-apoptosis activity once NF-kB was activated. The "super repressor" of NF-kB was constructed by deleting residues 356-498 in the middle region of murine p105 and C-terminal residues 800-971. The mutant did not generate p50 and is responsive to degradation stimuli. The p105(sr) retains the ability to interact with all NF-kB species, and inhibits TNF-α induced NF-kB activities.

p105(sr) was tested in a mouse skin papilloma MT1/2 cell line by transforming the cells with a nucleic acid having the sequence of SEQ ID NO. 5. p50 homodimer activity was significantly elevated in MT1/2 cells, and the cells were resistant to TNFα-mediated apoptosis. Repression of p50 homodimer activity and TNFα-mediated killing of these tumorigenic cells by p105(sr) was demonstrated. The results showed that p105(sr) is an effective NF-kB super repressor and can be used as a broader range alternative to IkBα(sr).

Results

Design and Generation of p105)sr) Although the C-terminal portion of p105, IKBγ, has been shown to co-immunoprecipitate p50, its affinity to other NF-kB species and even to p50 is not as high as the N-terminal RHD. The objective of the present invention was to design a super repressor based on p105, which contains both the RHD and the ankyrin repeats. For designing a p105-based NF-kB super repressor, two conditions must be satisfied. First, expression of the modified p105 should no longer generate p50, a component of the NF-kB transcription complex. Second, the modified p105 should not be degraded immediately upon extracellular signals, because such a process will release bound NF-kB species. Based on studies of regulation of p50/p105 homeostasis, it was decided to delete residues 356-498 in the middle-region that covers from the nuclear localization signal (NLS) to the putative degradation signal in the middle of p105 to disable p50 generation (FIG. 1A). To abolish signal-induced p105 degradation, residues 800-971 of p105 were deleted, which include the degradation signal in the C-terminus and the DD (FIG. 1A).

To test whether expression of this p105 mutant still generated p50, the p105(sr) construct was expressed in three different cell lines: 293, HeLa, and CHO-CD14. As demonstrated by immunoblotting with antibodies to the epitope tag gp10 attached at the N-terminus of p105(sr), expression of this mutant gene no longer generated p50 in any of the tested cells, whereas under the same condition, the wild-type p105 generates p50 normally (FIG. 1B).

Figure 2:
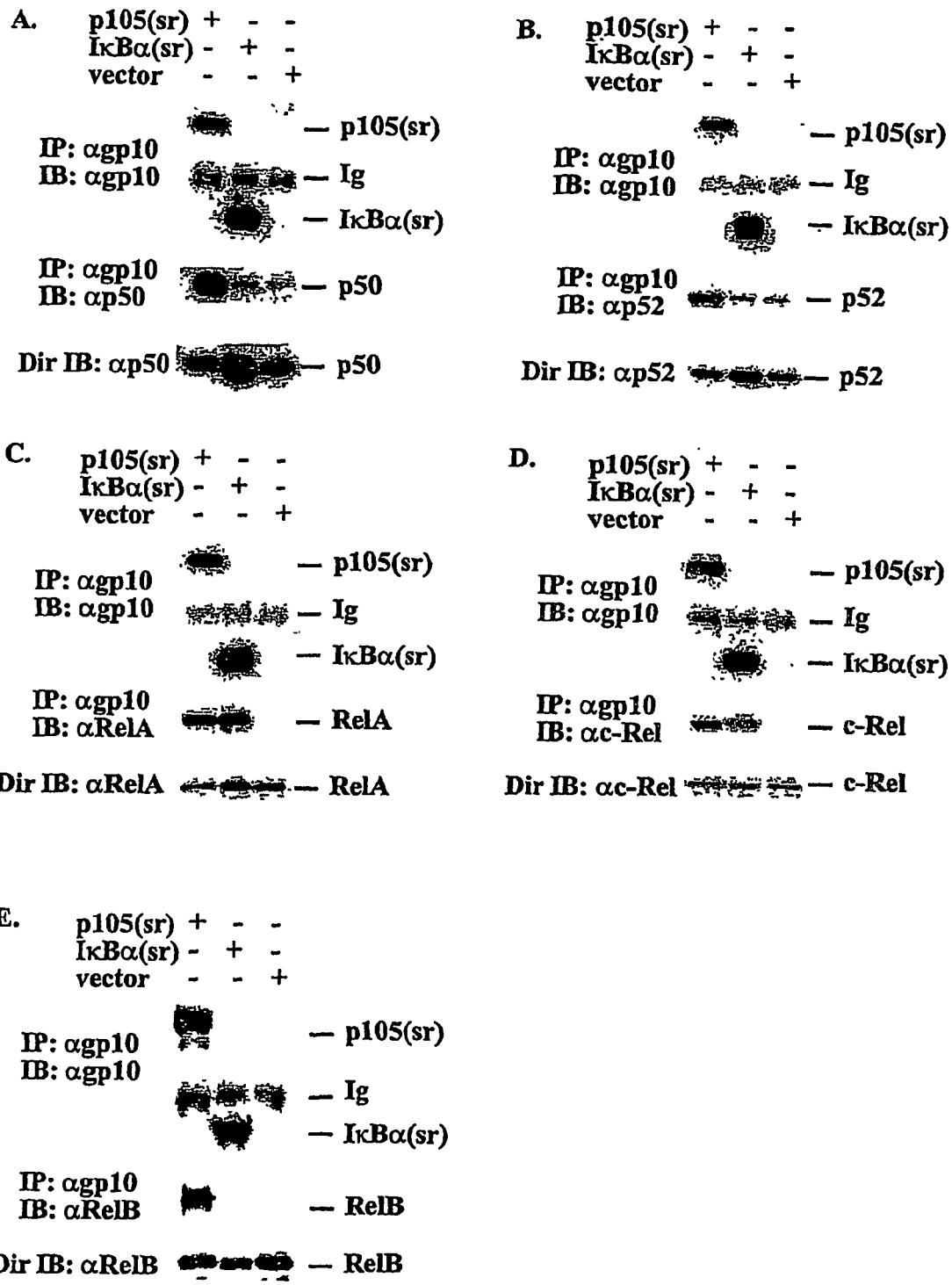
FIG. 2 (A-E). Co-immunoprecipitation of p105 (sr) with different NF-kB species. N-terminally tagged (with a gp10 epitope tag) p105(sr) or 1kBα(sr) were co-transfected with untagged NF-kB species to CHOCD14 cells. An empty vector was also co-transfected with these species as the negative control. The transfected cells were lysed, and the lysates were divided into two parts. One part was immunoprecipitated with anti-gp10 antibodies, and the precipitants were resolved with SDS PAGE (10%) and blotted either with anti-gp10 antibodies (top panels) or with antibodies specific to each NF-kB species (middle panels). To examine the expression of each specific NF-kB species, a portion of the second part of lysates (about 2.5 pg) was directly resolved with SDS PAGE (10%) and blotted with antibodies specific to each NF-kB species (bottom panels). Because of in vitro homologous recombination, p50 co-transfected with p105(sr) (both were cloned into and expressed from the same vector) resulted in a small portion of gp10-tagged p50 that migrated slightly faster than the IgG heavy chain (marked as an asterisk in A). IP, immunoprecipitation; IB, immunoblot.
Figure 3:
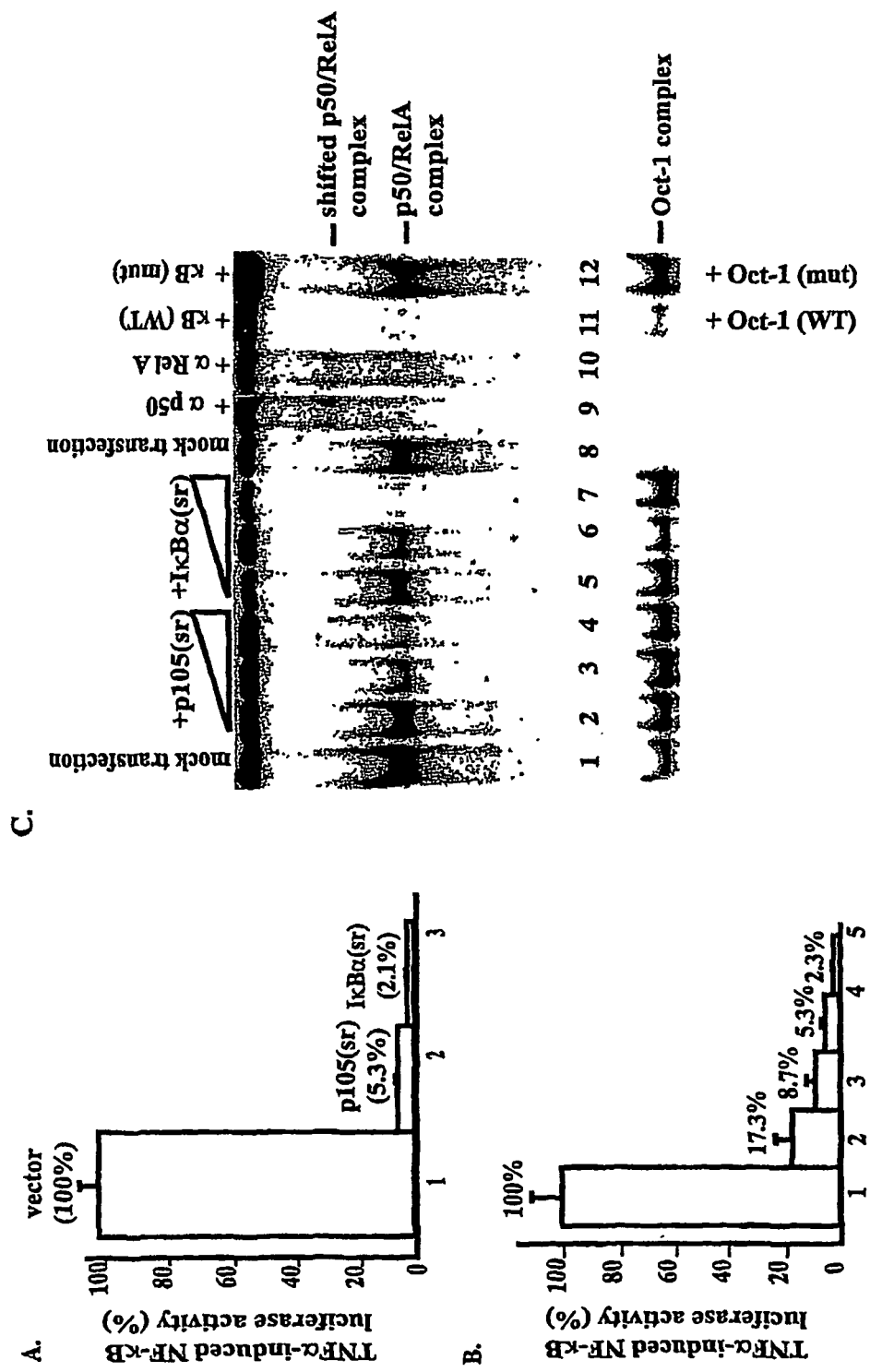
FIG. 3A. shows that p105(sr) represses TGN-α activity. Luciferase reporter assays on p105(sr) and IkBα(sr) 293 cells (10$^6$/well)/were co-transfected with 0.2 µg empty vector (column T), 1 KRndsrt (co/umn 2), or p105(sr) (column 3) and equal amounts of KB-frefl} luciferase construct. Thymidine kinase-Renilla Luciferase construct (0.05 µg) was included in all of the transfections as the internal control. The cells were treated with TNFα before being lysed for assay. The inhibitory effect by each super repressor was calculated as relative to luciferase activity from vector transfected cell lysates (as 100%), and all of the data were normalized with the readout of *Renilla* luciferase activity. Luciferase activity from vector-transfected cell lysates without treatment TNFα was used as the background reading and had been excluded from column 1.
FIG. 3B, p105(sr) repression is dose-dependent. 293 cells (10$^4$/well) were transfected with 0.05, 0.1, 0.2, and 0.4 µg of p105(sr) (columns 2-5, respectively) and the two luciferase vectors and assayed as described.
FIG. 3C, EMSA of TNFα-induced NF-kB activity. HeLa cells (106/well) were transfected with p105(sr) or IkBα (sr), and nuclear extracts were prepared from the cells 36 h post-transfection after treatment of with 20 ng/ml TNFα for 30 min. Lanes 1 and 8, vector-transfected: lanes 2-4, p105(sr)-transfected (0.1, 0.2, and 0.4 µg of DNA); lanes 5-7, IkBα (sr)-transfected (0.1, 0.2, and 0.4 µg of DNA); lane 9, super-shift with anti-p50 antibodies; lane 10, supershift with anti-RelA antibodies: lane 11, cold wild-type kB nucleotides competition: lane 12, cold mutant kB nucleotides competition. The lower panel shows binding of Oct-1 by the same lysates as the internal control (lanes 1-7) and cold wild-type and mutant Oct-1 nucleotides competition; lanes 11 and 12).

The response of p105(sr) to TNFα-induced degradation was tested. HeLa cells were transfected with either p105(sr) gene (SEQ ID NO. 1) or a p105 mutant of SEQ ID NO. 1, p105(Δ356-498), that carries the same middle region deletion but maintains an intact C terminus. The cells were metabolically labeled with [$^{35}$S]methionine/cysteine and chased with normal growth medium supplemented with TNFa. As shown in FIG. 1C, p105(sr) is more stable than p105(Δ356-498) upon TNFα treatment. Together, these results suggested that the designed p105(sr) is able to function as an effective NF-KB super repressor. In addition, the results in FIG. 1C also showed clearly that the degradation signal in the C-terminal portion of p105 is important for degradation of p105, whereas the degradation signal in the middle of p105 protein regulates p50 production.

p105(sr) Maintains the Ability to Interact with Rel/NF-kB Proteins. Because p105(sr) harbors two areas of deletion, it was not clear whether it maintained the ability to interact with Rel/NF-kB proteins. CHO-CD14 cells were co-transfected with p105(sr) and five different NF-KB species, p50, p52, RelA, c-Rel, and RelB. The transfected cells were lysed and immunoprecipitated with anti-gp10 antibodies first (co-immunoprecipitation), and the immunoprecipitants were then resolved with SDS-PAGE and immunoblotted with antibodies either to the gp10 tag or to the corresponding NF-kB protein. p105 maintained the ability to interact with all five NF-kB proteins (FIG. 2, left lanes). As reported previously by others, IkBα interacts with RelA and c-Rel only, and its interactions with p50, p52, and RelB are rather weak; IkB(sr), which carries the S32A,S36A mutation (a kind gift from Dr. Warner Greene's lab) with a similar gp10 epitope tag, co-immunoprecipitates RelA and c-Rel only and does not co-immunoprecipitate p50, p52, or RelB (FIG. 2, in middle lanes). Thus, p105(sr) maintains its ability to interact with all NF-kB species, demonstrating a broader inhibitory range than IkBα and the IkB(sr) mutant, neither of which interacts strongly with p50, p52, and RelB proteins.

p105(sr) Effectively Represses TNFa-induced NF-KB Activity. To test whether p105(sr) represses TNFα-induced NF-kB activity, p105(sr) was co-transfected with luciferase reporter constructs into 293 cells. The cell lysates were prepared and assayed for firefly luciferase activity, and the readouts were normalized with that of *Renilla* luciferase activity, which serves as the internal control. TNFα potently induced NF-kB dependent firefly luciferase activity in cells co-transfected with the reporters and empty expression vector (FIG. 3A, column 1). Such induction was significantly repressed by either p105(sr) or IkBα(sr) (FIG. 3A, columns 2 and 3). Repression of TNFα-induced NF-kB activity by p105(sr) is dependent upon the input of p-105(sr) (FIG. 3B). Similar results were obtained from TNFα-treated, p105(sr)-transfected HeLa cells.

Figure 4:
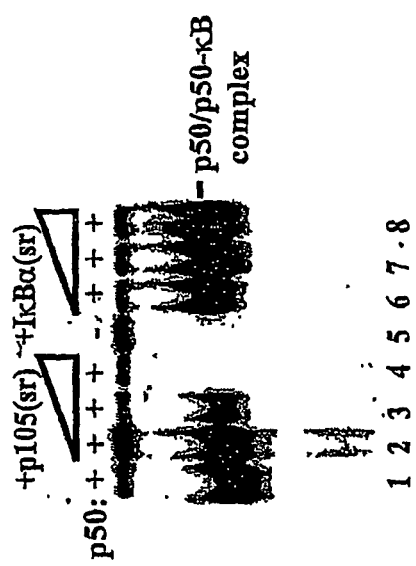
FIG. 4. p105(sr) effectively inhibits p50 homodimer. HeLa cells (10$^6$/well) were co-transfected with p50 (0.2 µg of DNA; lane 1) and p105(sr) (0.2, 0.4, and 0.6 µg of DNA; lanes 2-4), or p50 and IkBα(sr)(0.2, 0.4, and 0.6 µg; lanes 6-8, and nuclear extracts of transfected cells were prepared 36 h post-transfection for EMSAs. Lane 5. nuclear extracts from mock transfected cells.
Figure 5:
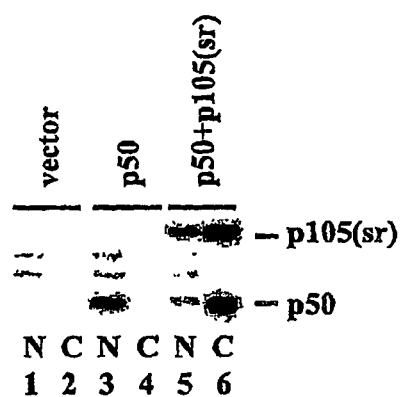
FIG. 5. Subcellular localization of p50/p105(sr) complex. CHOCD14 cells were transfected with the vector (0.3 µg), gp10-tagged p50 (0.3 µg), and gp10-p50 plus p105(sr) (0.3 and 0.9 µg, respectively), The transfected cells were then fractionated into cytoplasmic and nuclear portions. 2 µg of protein from each fraction were resolved with SDSPAGE and immunoblotted with anti-gp10 antibodies. N, nuclear fraction. C, cytoplasmic fraction FIG. 6A. Skin tumor cells exhibit elevated p50 homodimer activity and are resistant to apoptosis. Nuclear extracts of C50, MTU2, and CH 72T4 cells (lanes 1-3. respectively) were prepared, and 10-12 pg of extracts were subjected to EMSA. Upper panel, lanes 4-8, supershift of kB complexes with various anti-Rel protein antibodies: lanes 9 and 10, cold wild-type and mutant αB nucleotides competition, respectively. The lower panel shows binding of Oct-1 by the same lysates as the internal control (lanes 1-3).

To further assess the inhibitory function of p105(sr) further, HeLa cells were transfected with p105(sr) and then monitored the TNFα-induced NF-kB activities by EMSAs. Consistent with the luciferase assay, NF-kB activity was clearly inhibited in the nuclear extracts of p105(sr)-transfected cells (FIG. 3C, lanes 2-4). Because antibodies to either p50 or, RelA supershifted the detected NF-kB complex in EMSA (FIG. 3C, lanes 9 and 10), and the same complex diminished with increased input of p105(sr) or IKBn(sr) (FIG. 3C, lanes 5-7), it was concluded that p105(sr) effectively represses the prototypic NF-kB (p50/RelA) activity.

p105(sr) Is a Potent Repressor to p50 Homodimer Activity Although 1kBα(sr) is a potent repressor to RelA and c-Relcontaining NF-kB complexes, it does not inhibit activities of p50 or p52 homodimers and RelB containing complexes because of the weak interactions between IKBα and these proteins. It was then determined whether or not p105(sr) represses p50 homodimer activity by EMSAs. p50 and p105 (sr) were co-transfected into HeLa cells, and nuclear extracts from the transfected cells were prepared. Nuclear extracts from p50-transfected cells exhibited high p50 homodimer activity (FIG. 4, lane 1), and such activity was repressed by the increased input of p105(sr) (FIG. 4, lanes 2-4). In contrast, the increased input of IKBα (sr) did not affect p50 homodimer activity (FIG. 4, lanes 6-8).

p105(sr) Inhibits NF-kB Activity by Forming p105(sr/Rel Protein Heterodimeric Complex in the Cytoplasm—Wild-type p105 is located exclusively in the cytoplasm. It is not clear whether the deletions change the subcellular localization of p105(sr). To assess the mechanism of p105(sr)-mediated inhibition upon NF-KB activity, gp10-tagged p50 and p105(sr) were transfected into CHO-CD14 cells the cell lysates fractionated into nuclear and cytoplasmic portions. The two portions were resolved with SDS-PAGE and immunoblotted with antigp10 antibodies. Without p105(sr), p50 is largely located in the nucleus (FIG. 5, lane 3). However, when co-transfected with extra amounts of p105(sr), majorities of p50 were found in the cytoplasmic portion (FIG. 5, lane 6). Similar results were obtained in transfected 293 and HeLa cells. These results show that p105(sr) inhibits NF-KB activity by formation of the p105(sr)/Rel protein heterodimer in the cytoplasm.

p105(sr) Inhibits p50 Homodimer Activity in Skin Papilloma Cells and Facilitates TNFα-mediated Killing-Multistage carcinogen treatment of mouse skin results in papillomas, squamous cell carcinomas, and spindle cell carcinomas (a metastatic form of squamous cell carcinoma). In papilloma and squamous cell carcinoma tissues, the activity of p50 homodimer, rather than p50/RelA heterodimer, was found to be constitutively elevated. Mouse skin tumor cells were therefore chosen as a model system to test whether p105(sr) effectively represses endogenous p50 homodimer activity and whether such repression leads to effective killing of the tumor cells by TNFa.

To verify that in MT1/2 papilloma cells and CH72T4 carcinoma cells p50 homodimer activity is indeed constitutively elevated as observed previously in tissues (15), EMSAs were performed on nuclear extracts of these cells. As shown in FIG. 6A (lanes 2 and 3), CH72T4 and MT1/2 cells both exhibit elevated p50 homodimer activity. In contrast, p50 homodimer activity is not significantly elevated in nontumorigenic mouse skin cell line C50 (FIG. 6A, lane 1). Two closely migrated kB complexes were detected in the EMSAs. Anti-p50 antibodies shifted both complexes (FIG. 6A. lane 4), whereas anti-c-Rel antibodies shifted the slowly migrating complex only (FIG. 6A, lanes 5 and 7). Because the rest of antibodies did not shift these kB complexes (FIG. 6A, lanes 5, 6, and 8), it was concluded that these NF-kB complexes contain p50/c-Rel and p50/p50, respectively. Compared with p50 homodimer complex, the p50/c-Rel heterodimer complex appears to the minor species.

Figure 6:
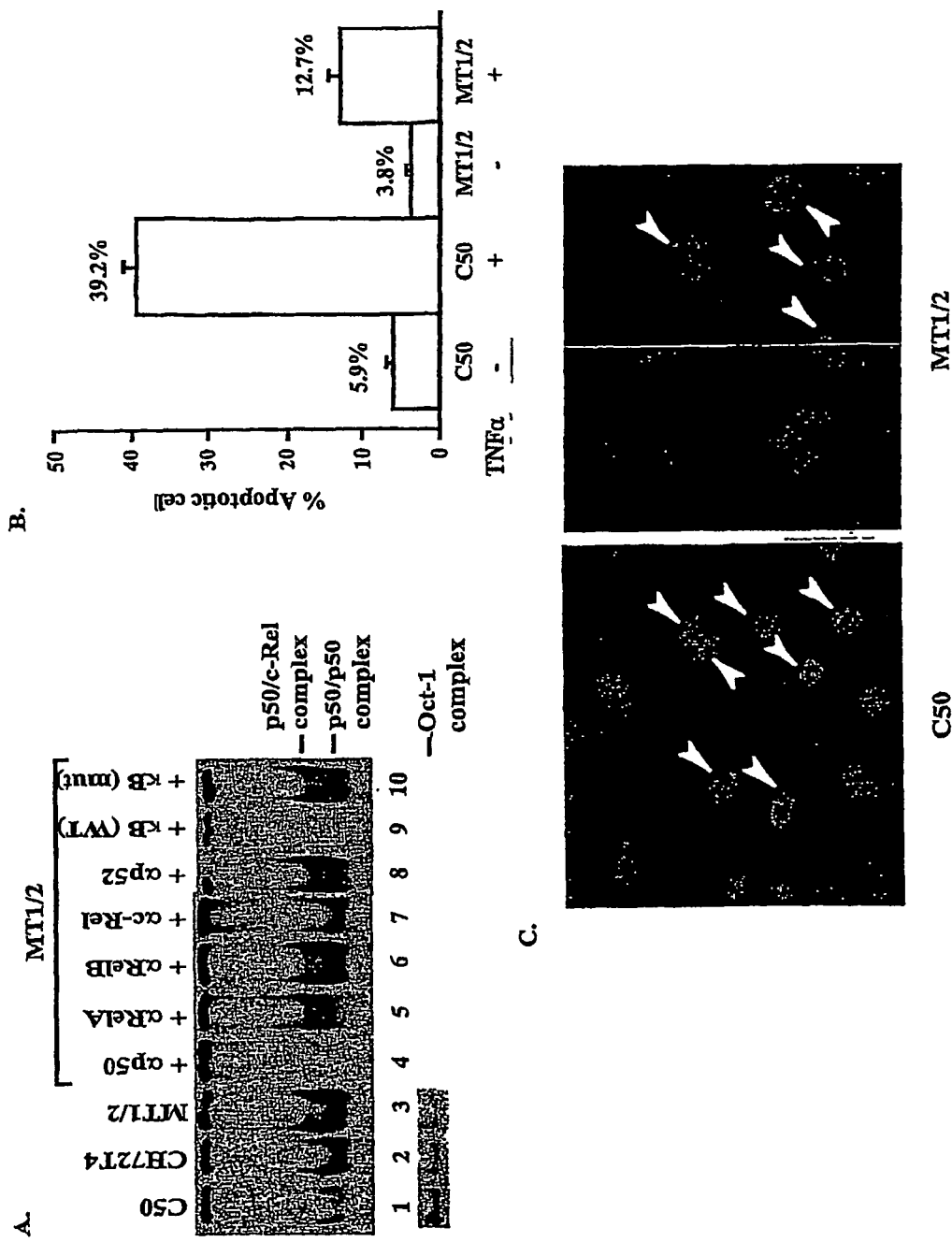
FIG. 6B, C50 and MT1/2 cells were treated with 20 mg/ml TNFα for 16 h. The cells were fixed, stained with Hoechst dye (33342), and examined with fluorescence microscope. The percentage of apoptotic cells was calculated by counting the apoptotic cells in eight randomly selected areas (each area contains ~100 cells). Chromosome condensation in the nuclei was used as a marker to score apoptotic cells, and the percentage of apoptotic cells (as cells mocked treated as controls) was calculated.
FIG. 6C, representative staining (Hoechst 33342) of TNFα-treated cells (the nuclei of the apoptotic cells are marked with arrows).
Figure 7:
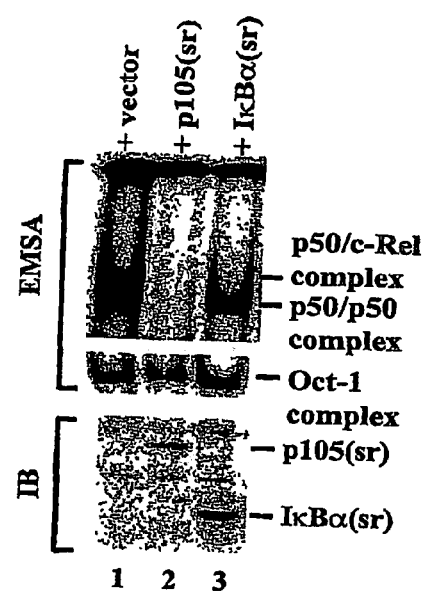
FIG. 7. p105(sr) represses NF-kB activities in skin papilloma cells. 1 µg of pEVRF expression vector, p105(sr), and IkBα (sr) (lanes 1-3, respectively) were transfected to MT1/2 cells preseeded in 6-well plate. The cells were harvested 24 h post-transfection, and the lysates were divided into two parts for EMSA and immunoblotting (IB) analyses. 10 pg of nuclear extracts were used for EMSA (upper and middle panels), and 10 µg unfractionated lysates were used for immunoblotting (lower panel).
Figure 8:
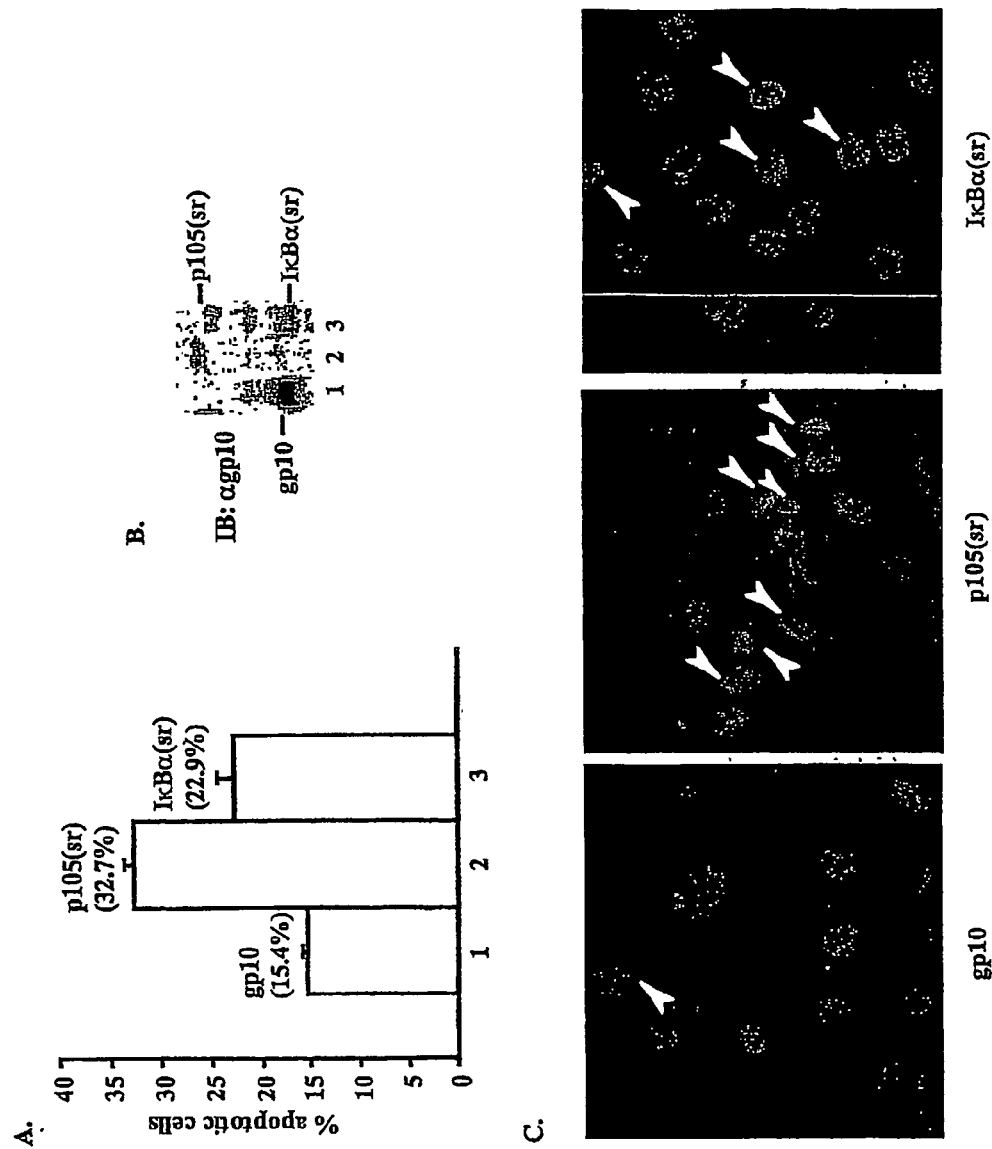
FIG. 8A. p105(sr) enhances TNFa-induced apoptosis. 1 pg of DNA vectors carrying gp10, p105(sr), or IkBα (sr) were transfected to 105 MT1/2 cells. At 30 h post-transfection, the cells were treated with TNFα for 16 h. The cells were then stained with Hoechst dye (33342) A, percentage of apoptotic cells.
FIG. 8B, representative staining (Hoechst 33342) of the transfected MTI/2 cells (the nuclei of the apoptotic cells are marked with arrows).
FIG. 8C, expression of transfected genes detected by immunoblotting (IB).

MT1/2 cells are also more resistant to TNFa-mediated killing than C50 cells. C50 and MT1/2 cells were treated with 20 μg/ml TNFa for 16 h, fixed with paraformaldehyde and stained with Hoechst dye. As shown in FIG. 6 (B and C). MT1/2 papilloma cells exhibit marked resistance to TNFα-induced apoptosis in comparison to the nontumorigenic C50 cells. A similar level of resistance was also found in CH72T4 cells.

p105(sr) or IkBα(sr) were transfected into MT1/2 papilloma cells and EMSAs performed. Similar to the co-transfection results shown in FIG. 4, p105(sr) effectively inhibits endogenous p50 homodimer and p50/c-Rel heterodimer activities in MT1/2 cells (FIG. 7, lane 2). In contrast. IkBα(sr) inhibits p50/c-Rel activity only (FIG. 7, lane 3).

p105(sr) was introduced into MTU2 cells to determine whether or not it would enhance TNFα-mediated apoptosis. As shown in FIG. 8 (A, columns 2 and 3, and B), p105(sr) and IkBα(sr) both facilitate TNFα-mediated apoptosis in MT1/2 cells, with p105(sr) consistently exhibiting a more effective enhancement than IkBα(sr). Such a difference is statistically significant (Student's t test, $p<0.05$). The enhancement of TNFα-mediated killing by the super repressors in MT1/2 appears to be specific rather than the nonspecific toxicity caused by expression of an exogenous protein, because expression of a full-length gp10 only slightly affects the cell death (FIG. 8, A and B). Because p105(sr) inhibits all NF-kB activities, whereas IKBα(sr) represses RelA and c-Rel containing NF-kB activities only. Thus, p50 homodimer activity, although it may not be the sole anti-apoptotic resource, is at least partially responsible for the survival of skin tumor cells.

Discussion

The NF-kB family consists of five different members, all of which can form various homo and heterodimers. This family of transcription factors regulates cell growth and developmental processes and is a component of innate immunity network. Persistent activation of NF-kB often occurs during inflammation and other pathological conditions such as cancers and pathogen infections. Inhibition of NF-kB therefore helps to circumvent or ease these conditions. Inhibition of NF-kB also facilitates drug- and chemotherapy reagent-mediated cell killing. Although an IkBα-based super repressor and various small chemical-based inhibitors repress NF-kB activities, they mainly target RelA and c-Rel complexes, and do not affect other NF-kB complexes, such as p50 and p52 homodimers, and RelB heterodimers. In most cells, the p50/RelA heterodimer is the prototypical and dominant complex. However, other atypical NF-kB complexes also participate in cellular regulations, and dysregulation of these atypical species under pathological conditions has been reported.

The present invention involves the design generation, and testing of a p105-based super repressor on the basis of the current knowledge of the mechanism of p50/p105 homeostasis. This p105-based super repressor broadly and effectively inhibits all NP-kB activities in the cell. The novel p105(sr) can be used as an adjuvant for anti-inflammatory, anti-cancer drugs and chemotherapy reagents to increase the killing of inflamed and cancerous cells. This application may be particularly useful for tissues where atypical NF-kB activities are dominant or when multiple NF-kB complexes are activated. Because many of the downstream products of atypical NF-kB transcription complexes are unknown, introducing p105(sr) into a cell in combination with DNA microarray analyses will allow systematic dissection of gene targets leading to a clearer understanding of the role of various NF-kB species in cell development and pathogenesis. Revealing the identity of these target genes will also help future development and design of drugs against inflammatory diseases and cancers.

The correlation of the significant elevation of p50 homodimer activity and resistance to apoptosis in marine B cell lymphomas is recognized. The present studies found strong resistance to TNFα-induced apoptosis in MT1/2 (FIG. 6) as well as in CH72T4 skin cancer cells. Hence, development of p105(sr) may provide an effective means to curtail p50 homodimer activity and facilitate apoptosis in these cancer cells. As disclosed herein, introducing p105(sr) into MTI/2 papilloma cells significantly enhances TNFα-mediated killing (FIG. 8). In EMSA, p105(sr) appears to repress both p50 homodimer and p50/c-Rel heterodimer activity in MT1/2, whereas IkBα(sr) inhibits the minor p50/c-Rel heterodimer activity only (FIG. 7, lanes 2 and 3). However, in apoptosis analyses, the difference of apoptotic enhancement between p105(sr) and IkBα(sr) is less dramatic (32.7% versus 22.9%; FIG. 8A). TNFα induces prototypic RelA/p50 heterodimer activity, which is the primary inhibitory target of IkBα(sr). Although p50 homodimer activity is constitutively elevated in MT1/2 cells and may contribute to sustained growth of the skin papilloma cells, it accounted for only a portion of the anti-apoptotic functions. This portion of anti-apoptotic functions exerted by p50 homodimer, however, is significant and cannot be repressed by IkBα(sr), which inhibits RelA and c-Rel-related NF-kB activities. The fact that p105(sr) is consistently more effective than IkBα(sr) in apoptosis enhancement clearly supports this view. p105(sr) with its broad inhibitory range, is more effective than IkBα(sr) and may serve as a better candidate for a chemotherapy adjuvant to treat cancer cells where atypical NF-kB activity is dominant or multiple NF-kB activities are detected. Together, these studies suggest that p105(sr), like IkBα(sr), can function as an effective NF-kB surrogate in a physiological environment.

A slightly stronger inhibitory effect by IkBα(sr) than by p105(sr) in luciferase reporter assays and EMSAs (FIG. 3) was consistently observed. Such a difference may be due to different inhibitory mechanisms exerted by these two repressors. IkBα binds RelA in the NF-kB dimeric complex directly, forming a ternary complex, and is able to shuttle between the cytoplasm and the nucleus. Thus, introducing IkBα(sr) into the cell may render immediate repression of NF-kB activities. In contrast, p105 binds to individual NF-kB/Rel protein, forming a p105/Rel protein heterodimer in the cytoplasm. Because of the strong association of the Rel homology domains, the dissociation rate of a preformed NF-kB complex (especially a heterodimer) in vivo may be rather slow. Hence, p105(sr) is likely to target the newly synthesized NF-kB members rather than the preformed NF-kB complexes. Indeed, repression of NF-kB by p105(sr) in 12 h post-transfection measured by both luciferase reporter assays and EMSAs was not as robust as that of 36-48 h post-transfection, suggesting a slight leak of repression in the early phase. Because p105(sr) is overexpressed in the cell, and its natural turnover is slower than that of IkBα (sr), an effective repression by p105(sr) in the late phase (FIGS. 3 and 4) can still be achieved.

Although the wild-type p105 resides exclusively in the cytoplasm, a fraction of p105(sr) was found in the nucleus, despite the lack of the NLS in this p105 mutant (FIG. 5, lanes 5 and 6). Because p50 was well fractionated in p50-transfected cells by the same method (FIG. 5, lanes 3 and 4), it is unlikely that p105(sr) detected in the nucleus was due to incomplete fractionation. In addition, nuclear localization of p105(sr) is not dependent upon binding to p50, which contains the NLS, because p105(sr) was also being detected in the nucleus when the cell was transfected by p105(sr) alone. It has been suggested that the DD in the C-terminus of p105, in addition to the NLS, participates in regulation of the subcellular localization of p105. Lack of DD in p105(sr) may therefore be responsible for its localization in the nucleus. Another version of p105(sr), which includes the NLS and has similar inhibitory effect in the cell, exhibits increased nuclear localization. Because p105 also interferes with NF-κB binding to the kB sequences, translocation of p105(sr)/Rel protein complexes into the nucleus will not result in transcription activation.

It has not been determined whether p105(sr) inhibits p52 homodimer or RelB heterodimer activity, although both proteins were found to co-immunoprecipitate with p105(sr) (FIG. 2, B and E), indicating that similar repression of p52 and ROB activities can be achieved. Constitutive processing generates a low level of p52 in the cell, and production of p52 is greatly enhanced by stimulation of a subset of cytokines. Deregulation of nfkb2 genes also results in malignancy, and inhibition of abnormal p52 homodimer activity may be of significant importance. Studies have shown that both constitutive and induced p52 generation require de novo protein synthesis, implying a co-translational mechanism during the process. Given that p105(sr) is likely to target nascent Rel proteins, it is possible to repress p52-related activity by formation of the p105(sr)/p52 complex. On the other hand, when the mechanism of p100/p52 regulation becomes clear, design and generation of a p100-based repressor that specifically targets p52 is also possible.

EXAMPLES

Example 1

Construction of p105(sr)—

PCR was used to generate two deletions within murine ntkbl gene. Two sets of primers were used to generate deletion in the middle region first: 5'-CGGGATCCATGGCAGAC-GATG, SEQ ID NO. 9 and 5'-CCCAAGCTTTTC-CTCTTTGTCTTTGATTTC (SEQ ID NO. 10) to amplify the first half of nfrkbl and 5'-GACTAGTAAGGCTCTG-CAGCTCGCC (SEQ ID NO. 11) and 5'-GCTCTAGAC-TAAATTTTGCCTTCAATAGG (SEQ ID NO. 12) to amplify the second half of the gene. The DNA fragments were cloned into the expression vector pEVRF, with a blunted Hind III site from the first fragment directly ligated to the uncut 5'-end of the second fragment to preserve the correct reading frame. The above plasmid was then used as the template, and the primers 5'-CGGGATCCATGGCAGACGATG (SEQ ID NO. 13) and 5'-GGAATTCGGATCCTGGTAGTATATCAT-CAG (SEQ ID NO. 14) were used for PCR. The PCR fragment was subsequently cloned into a modified pEVRF that attaches a 12-residue epitope tag from the bacterial phage T7 gene 10 protein at the N-terminus of the expressed protein.

Example 2

Cell Culture Aid Transfection

Human embryonic kidney 293 cells, human cervical carcinoma HeLa cells, Chinese hamster ovary cells with a stably transfected human CD14 surface marker (CHO-CD14), and several mouse skin cell lines were used in the studies. HeLa and 293 cells were cultured in Dulbecco's modified Eagle's medium supplemented with 10% fetal bovine serum, 2 mM L-glutamine, and antibiotics and CHO-CD14 cells in RPM1640 medium with the same supplements. The cells were seeded in either 24- or 6-well plates and transfected with LipofectAMINE (Invitrogen) according to the manufacturer's instructions. Skin papilloma cell line MTI/2, carcinoma line CH72T4 (spindle cell carcinoma), and the control keratinocyte line C50 were cultured in minimum essential Eagle's medium with Earle's balanced salt solutions supplemented with 4% (for MT1/2) or 1% (for C50 and CH72T4) fetal bovine serum, L-glutamine, antibiotics, and other growth supplements. The skin cells were transfected with FuGENE 6 (Roche Applied Science) according to the manufacturer's instructions.

Example 3

Measurement of Protein Concentration

A Bio-Rad protein concentration kit was used according to the manufacturer's instructions, with bovine serum albumin as the standard.

Example 4

Immunoblotting and Co-immunoprecipitation

Transfected CHO-CD14 cells were harvested 12-24 h post-transfection, and lysed with ELB buffer (300 mM NaCl, 0.1% Nonidet P-40, 50 mM Tris-HCl (pH 7.5), 5 mM EDTA, 1 mM phenylmethylsulfonyl fluoride, and 1 mM dithiothreitol). For direct immunoblottings, 2-3 μg of lysates were resolved with SDS-PAGE (10%) and transferred to Immobilon-P membrane (Millipore). The membrane was blotted with antibodies, and the reactive bands were detected with ECL reagents (Amersham Biosciences). For co-immunoprecipitations followed with immunoblottings, expression vectors carrying gp 10-tagged p105(sr) or IkBα(sr), and the testing NF-kB species were co-transfected into CHO-CD14 cells, and the lysates were first immunoprecipitated with anti-gp 10 monoclonal antibodies (Novagen) and protein A-Sepharose CL-4B beads (Sigma) at 4° C. for 3 h to overnight (rotating). The protein A beads were then washed several with ELB buffer containing 1 M NaCl and suspended in SDS gel loading buffer. After boiling, the supernatants were resolved with SDS-PAGE, transferred to Immobilon-P membrane, and blotted with antibodies either to gp 10 or to the NF-kB species (rabbit polyclonal: Santa Cruz Biotechnology).

Example 5

Pulse-Chase Metabolic Labeling

Transfected HeLa cells were preincubated with Dulbeccos modified Eagle's medium without methionine and cysteine for 1 h and pulse-labeled with 10 pCi/ml [$^{35}$S]methionine/cysteine (Perkin Elmer Life Sciences) for 30 min following immunoprecipitation as described previously.

Example 6

Luciferase Reporter Assay 293 or HeLa cells (105 in 24-well plate) were co-transfected with either p105(sr) or IkBα(sr), with two luciferase reporter constructs: kB-luciferase (firefly) construct and thymidine kinase-Renillo luciferase construct. (Promega). The latter reporter driven by a thymidine kinase promotor provides a low level, constitutive expression of Renillo luciferase in the cell and hence serves as the internal control. 36 h post-transfection, the transfected cells were treated with TNFα (20 μg/ml) for 30 min and lysed. The lysates were then assayed with luciferase substrates provided by the Promega kit. For each experiment, lysates from three independently transfected cells were assayed, and all of the data were normalized with the readout of *Renilla* luciferase activity.

Example 7

Electrophoretic Mobility Shift Assay (EMSA)

100 ng of doublestranded kB probe (Santa Cruz Biotechnology) was labeled with 15 pCi of [γ-$^{32}$P]ATP (Amersham Biosciences) and T4 polynucleotide kinase and purified with MicroSpin G-50 mini columns (Amersham Biosciences). 8 μg of TNFα-treated or 2.5 μg of p50-transfected HeLa cell nuclear extracts were incubated with I μg of poly(dI-dC), 1 μg of labeled kB probe, and the binding buffer (10 mM Tris.HCl, pH 8.0, 150 mM KCl, 0.5 mM EDTA. 0.1% Triton X-100, 12.5% glycerol, and 0.2 mM dithiothreitol) at room temperature for 30 min before loading to 5% nondenaturing polyacrylamide gel. For antibody-mediated supershift, the reaction mixture was preincubated with I μl of either anti-p50 or anti-RelA antibodies (Santa Cruz Biotechnology) at room temperature for 20 min before loading of the samples. For cold kB nucleotide competition, 20 ng of the wild-type or mutant KB nucleotides were preincubated with the reaction mixture.

Example 8

Cell Fractionation

Transfected CHO-CD14 cells ($2\times10^7$) were lysed with sucrose buffer (0.32 M sucrose, 10 mM Tris.HCl pH 8.0, 3 mM CaCl$_2$, 2 mm MgOAc, 0.1 mM EDTA, 0.5% Nonidet P-40, I mM dithiothreitol, and 0.5 mM phenylmethylsulfonyl fluoride) and centrifuged at 500×g for 5 min. The supernatants were saved as the cytosolic fraction. The pellets were washed once with sucrose buffer without Nonidet P-40 and suspended in low salt buffer (20 mM HEPES. pH 7.9, 1.5 mM MgCl$_2$, 20 mM KCl, 0.2 mM EDTA, 25% glycerol, 0.5 mM dithiothreitol, and 0.5 mM phenylmethylsulfonyl fluoride). An equal volume of high salt buffer (same composition as the low salt buffer except with 800 mM KCl) was added slowly. The lysates were incubated for 30-45 min at 4° C. on a rotator and centrifuged at 14,000×g for 15 min. The supernatants were saved as nuclear fractions.

Example 9

Apoptosis Assays

MT1/2 and C50 cells were treated with TNFα (20 μg/ml) for 16 h. The cells were washed with phosphate-buffered saline buffer and fixed with 4% r paraformaldehyde for 30 min at room temperature. The cells were then stained with 5 μg/ml of Hoechst dye (32324, Sigma) for 10 min and examined with fluorescence microscopy. The percentage of cells undergoing apoptosis was calculated by counting apoptotic cells in eight random areas (each area contains approximate 100 cells) of each treated sample as previously reported. The data represent three sets of separated experiments. Similar analyses were applied to transfected MT1/2 cells.

While the various embodiments of the present invention have been described in detail, it is apparent that modifications and adaptations of those embodiments will occur to those of skill in the art. It is to be understood that such modifications and modifications are within the scope of the invention, as set forth in the following claims.

References
1. Baldwin, A. S., Jr. (1996) *Anna. Rev. Immunol.* 14, 649-683
2. Chen, L., Fischle, W., Verdin, E., and Greene, W. C. (2001) *Science* 293, 1653-1657

3. Sun, S. C., Ganchi, P. A., Ballard, D. W., and Greene, W. C. (1993) *Science* 259, 1912-1915
4. Gilmore, T., Gapuzan M. E., Kalatzidis, D., and Starczynowski, D. (2002) *Cancer Lett.* 181, 1-9
5. Karin, M., Cao, Y., Greten, F. R., and Li, Z. W. (2002) *Nat. Rev. Cancer* 2, 301-310
6. Karin, M., and Lin, A. (2002) *Nat. Immunol.* 3, 221-227
7. Lin, A., and Karin, M. (2003) *Semin. Cancer Biol.* 13, 107-114
8. Rayet, B., and Gelinas, C. (1999) *Oncogene* 18, 6938-6947
9. Wang, C. Y., Mayo, M. W., and Baldwin, A. S., Jr. (1996) *Science* 274, 784 787
10. Wang, C. Y., Cusack, J. C., Jr., Li R., and Baldwin, A S., Jr. (1999) *Nat. Med.* 5, 412-417
11. Baldwin, A. S. (2001), *J. Clin. Invest.* 107, 241-246
12. Hinz, M., Lemke, P., Anagnostopoulos, I. Hacker, C., Krappmann D., Mathas, S., Dorken, B., Zenke, M., Stein, H., and Scheidereit, C. (2002) *J. Exp. Med.* 196, 605-617
13. Chen, Z., Hagler. J. Palombella, V. J., Melandri, F., Scherer, D., Ballard, D., and Maniatis T. (1995) *Genes Dev.* 9, 1586-1597
14. Pomerantz, J. L., and Baltimore, D. (2002) *Mol. Cell* 10, 693-695
15. Budunova, I. V., Perez, P., Vaden. V. R., Spiegelman, V. S., Slaga. T. J., and Jorcano, J. L. (1999) *Oncogene* 18, 7423-7431
16. Kurland, J. F., Kodym, R., Story, M. D. Spurgers, K. B., McDonnell, T. J., and Meyn, R. E. (2001) *J. Biol. Chem.* 276, 45380-45386
17. Cogswell, P. C., Guttridge D. C., Funkhouser, W. K, and Baldwin, A. S., Jr. (2000) *Oncogene* 19, 1123-1131
18. Hatada, E. N., Nieters, A., Wulczyn. F. G., Naumann, M., Meyer, R., Nucifora, G., McKeithan, T. W., and Scheidereit, C. (1992) *Proc. Natl. Acad. Sci. U.S.A.* 89, 2489-2493
19. Hatada, E. N., Naumann, M., and Scheidereit, C. (1993) *EMBO J.* 12, 2781-2788
20. Liou, H. C., Non G. P., Ghosh, S., Fujita, T., and Baltimore, D. (1992) *EMBO J.* 11, 3003-3009
21. Naumann, M., Wulczyn. F. G., and Scheidereit, C. (1993) *EMBO J,* 12, 213-222
22. Moorthy, A. K., and Ghosh, G. (2003) *J. Biol. Chem.* 278, 556-566
23. Lin, L., DeMartino, G. N., and Greene, W. C. (1998) *Cell* 92, 819-828
24. Lin, L., DeMartino, G. N., and Greene, W. C. (2000) *EMBO J.* 19, 4712-4722
25. Heissmeyer, V., Krappmann, D., Hatada B. N., and Scheidereit, C. (2001) *Mol. Cell. Biol.* 21, 1024-1035
26. Beinke, S., Belich, M. P., and Ley, S. C. (2002) *J. Biol. Chem.* 277, 24162-24168
27. Heissmeyer, V., Krappmann, D., Wulczyn, F. G., and Scheidereit, C. (1999) *EMBO J.* 18, 4766-4778
28. Salmeron, A., Janzen J., Soneji Y., Bump, N., Kamens, J., Allen. H., and Ley, S. C. (2001) *J. Biol. Chem.* 276, 22215-22222
29. Lin, L., and Ghosh. S. (1996) *Mol. Cell. Biol.* 16, 2248-2254
30. Orian, A., Schwartz, A. L., Israel, A., Whiteside, S., Kahana, C., and Ciechanover. A. (1999) *Mol. Cell. Biol.* 19, 3664-3673
31. Spiegelman, V. S., Budunova, I. V, Carbajal, S., and Slaga, T. J. (1997) *Mol. Cacinog.* 20, 99-107
32. Ghosh, S., Gifford, A. M., Riviere, L. R., Tempst, P., Nolan. G. P., and Baltimore, D. (1990) *Cell* 62, 1019-1029
33. Matthias, P., Muller, M. M., Schreiber, E., Rusconi. S., and Schaffner, W. (1989) *Nucleic Acids Res.* 17, 6418
34. Dunn, J. J., and Studier, F. W. (1983) *J. Mol. Biol.* 166, 477-535
35. Kirkland, T. N., Finley, F., Leturcq, D., Moriarty, A., Lee, J. D., Ulevitch, R. J., and Tobias, P. S. (1993) *J. Biol. Chem.* 268, 24818-24823
36. La, E., Muga, S J. Locniskar, M. F., and Fischer, S. M. (1999) *Mol. Carcinog.* 24, 276-286
37. Tang, G., Yang, J., Minemoto, Y., and Lin, A. (2001) *Mol. Cell.* 8, 1005-1016
38. Tang, F., Tang. G., Xiang, J., Dai, Q., Rosner, M. R., and Lin, A. (2002) *Mol. Cell. Biol.* 22, 8571-8579
39. Inoue, J., Kerr, L. D., Kakizuka, A., and Verma, I. M. (1992) *Cell* 68, 1109-1120
40. Rice, N. R., MacKichan, M. L., and Israel, A. (1992) *Cell* 71, 243-253
41. Ernst, M. K. Dunn, L. L., and Rice, N. R. (1995) *Mol. Cell. Biol.* 15, 872-882
42. Urban, M. B., and Baeuerle, P. A. (1990) *Genes Dev.,* 4, 1975-1984
43. Slaga, T. J., Budunova, I. V., Gimenez-Conti, I. B., and Aldaz, C. M. (1996) *J. Investig. Dermatol. Symp. Proc.* 1, 151-156
44. Hatada, E. N., Krappmann. D., and Scheidereit, C. (2000) *Curr. Opin. Immunol.* 12, 52-58
45. Medzhitov, R., and Janeway, C., Jr. (2000) *Immunol. Rev.* 173, 89-97
46. Kurland. J. F., Voehringer, D., W., and Meyn, R. E. (2003) *J. Biol. Chem.* 278, 32465-32470
47. Baeuerle, P. A., and Baltimore, D. (1989) *Genes Dev.* 3, 1689-1698
48. Sachdev, S., Bagchi, S., Zhang, D. D., Mings, A. C., and Hannink, M. (2000) *Mol. Cell. Biol.* 20, 1571-1582
49. Heusch, M., Lin, L., Geleziunas, R., and Greene, W. C. (1999) *Oncogene* 18, 6201-6208
50. Betts, J. C., and Nabel, G. J. (1996) *Mol. Cell. Biol.,* 16, 6363-6371
51. Caamano, J. H., Rizzo, C. A., Durham, S. K., Barton, D. S., Raventos-Suarez, C., Snapper, C. M., and Bravo, R. (1998) *J. Exp. Med.* 187, 185-196
52. Franzoso, G., Carlson, L., Poljak, L. Shores, E. W., Epstein, S., Leonardi, A., Grinberg, A., Tran, T., Scharton-Kersten, T., Anver, M., Love, P., Brown, K., and Siebenlist, U. (1998) *J. Exp. Med.* 187, 147-159
53. Claudio, E., Brown, K., Park, S., Wang. H., and Siebenlist, U. (2002) *Nat. Immunol.* 3, 958-965
54. Mordmuller, B., Krappmann, D., Esen, M., Wegener, E., and Scheidereit. C. (2003) *EMBO Rep.* 4, 82-87

What is claimed is:

1. An isolated modified nuclear factor kappa B (NF-κB) repressor polypeptide comprising the amino acid sequence of SEQ ID NO: 6 or SEQ ID NO: 8.

2. The isolated modified nuclear factor kappa B (NF-κB) repressor polypeptide of claim 1, wherein said polypeptide is encoded by the polynucleotide of SEQ ID NO: 5 or SEQ ID NO: 7.

3. The isolated modified nuclear factor kappa B (NF-κB) repressor polypeptide of claim 1, wherein said polypeptide comprises the amino acid sequence of SEQ ID NO: 6.

4. The isolated modified NF-κB repressor polypeptide of claim 1, wherein said polypeptide comprises the amino acid sequence of SEQ ID NO: 8.

* * * * *

SEQUENCE LISTING

<160> NUMBER OF SEQ ID NOS: 14

<210> SEQ ID NO 1
<211> LENGTH: 3892
<212> TYPE: DNA

<213> ORGANISM: Mus musculus
<220> FEATURE:
<221> NAME/KEY: modified_base
<222> LOCATION: (3755)
<223> OTHER INFORMATION: a, t, c or g

<400> SEQUENCE: 1

| | | | | | | |
|---|---|---|---|---|---|---|
| agcggccgcc | gcgggcgcgc | tctagcagcg | caggccggag | ctcagggccc | cgcgcgcccg | 60 |
| gcccgccccg | cgcttctccg | cccgcgccgc | agccatggcg | cgccgctgag | ccgcccgccc | 120 |
| gcccgcccgc | gccccgaccc | ggctcggctc | ccgccggtcc | gcgccgctcc | gcagcggagc | 180 |
| ccgcaggcga | ggagaggccg | cgcgcatctc | cagggtaccc | tcagaggcca | gaagagggtg | 240 |
| tcagagccct | tgtaactgga | gtttgacggt | cgtgagctgc | gcatcttcac | catggcagac | 300 |
| gatgatccct | acggaactgg | gcaaatgttt | catttgaaca | ctgctttgac | tcactcaata | 360 |
| tttaatgcag | aattatattc | accagaaata | ccactgtcaa | cagatggccc | ataccttcaa | 420 |
| atattagagc | aaccaaaaca | gaggggattt | cgattccgct | atgtgtgtga | aggcccatca | 480 |
| cacggagggc | ttccgggagc | tctagtgag | aagaacaaga | aatcctaccc | acaggtcaaa | 540 |
| atttgcaact | atgtggggcc | tgcaaaggtt | atcgttcagt | tggtcacaaa | tggaaaaaac | 600 |
| atccacctgc | acgcccacag | cctggtgggc | aagcactgtg | aggacggggt | atgcaccgta | 660 |
| acagcaggac | ccaaggacat | ggtggttggc | tttgcaaacc | tgggaatact | tcatgtgact | 720 |
| aagaaaaagg | tatttgaaac | actggaagca | cggatgacag | aggcgtgtat | tagggctat | 780 |
| aatcctggac | ttctggtgca | ttctgacctt | gcctatctac | aagcagaagg | cggaggagac | 840 |
| cggcaactca | cagacagaga | gaaggagatc | atccgccagg | cagccgtgca | gcagaccaag | 900 |
| gagatggacc | tgagcgtggt | gcgcctcatg | ttcacagcct | tcctccctga | cagcactggc | 960 |
| agcttcactc | ggagactgga | gcctgtgtg | tcagacgcca | tctatgatag | caaagccccg | 1020 |
| aatgcatcca | acctgaaaat | cgtgagaatg | acagaacag | caggatgtgt | gacgggaggg | 1080 |
| gaggagattt | accttctctg | tgacaaggtt | cagaaagatg | acatccagat | tcggttttat | 1140 |
| gaagaggaag | aaaatggcgg | agtttgggaa | ggatttgggg | acttttcccc | cacggatgtt | 1200 |
| catagacagt | ttgccattgt | cttcaaaacg | ccaaagtata | aggatgtcaa | cattacaaag | 1260 |
| ccagcttccg | tgtttgttca | gcttcggagg | aaatcagacc | tggaaactag | tgaaccgaaa | 1320 |
| cccttttctct | actaccctga | aatcaaagac | aagaggaag | tgcaaaggaa | acgccagaag | 1380 |
| cttatgccga | acttctcgga | cagcttcggc | ggcggcagtg | gagcgggagc | cggtggtgga | 1440 |
| ggcatgttcg | gtagtggcgg | tggcggaggg | agtaccggaa | gccctggccc | agggtatggc | 1500 |
| tactcgaact | acggatttcc | tccctacggt | gggattacat | tccatcccgg | agtcacgaaa | 1560 |
| tccaacgcag | gggtcaccca | tggcaccata | aacaccaaat | ttaaaaatgg | ccctaaagat | 1620 |
| tgtgccaaga | gtgatgacga | ggagagtctg | actctccctg | agaaggaaac | tgaaggtgaa | 1680 |
| gggcccagcc | tgcccatggc | ctgcaccaag | acggaaccca | tcgccttggc | atccaccatg | 1740 |
| gaagacaagg | agcaggacat | gggatttcag | gataacctct | ttctcgagaa | ggctctgcag | 1800 |
| ctcgccaggc | gacacgccaa | cgccctttc | gactacgcag | tgacggggga | tgtgaagatg | 1860 |
| ttgctggccg | tgcaacgcca | tctcaccgcc | gtgcaggatg | agaatgggga | cagtgtctta | 1920 |
| cacttagcca | tcatccacct | ccacgctcag | ctcgtgaggg | atctgctgga | agtcacatct | 1980 |
| ggtttgatct | ctgatgacat | catcaacatg | agaaatgacc | tgtatcagac | acctctgcac | 2040 |
| ttggccgtga | tcaccaagca | ggaagatgta | gtagaggatt | tgctgagggt | tggggctgac | 2100 |
| ctgagccttc | tggaccgctg | gggcaactct | gtcctgcacc | tagctgccaa | agaaggacac | 2160 |

-continued

```
gacagaatcc tcagcatcct gctcaagagc agaaaagcag cgccccttat cgaccacccc    2220
aatggggaag gtctaaatgc catccacata gctgtgatga gcaatagcct gccatgtctg    2280
ctgctgctgg tggctgccgg ggcagaagtc aatgctcagg agcagaagtc tgggcgcacg    2340
ccgctgcacc tggccgtgga gtacgacaac atctccttgg ctggctgcct gcttctggag    2400
ggtgatgccc acgtggacag taccacctat gatgggacta cacctctgca tatagcggcc    2460
ggaagagggt ccaccagact ggcagctctt ctcaaagcag caggagcaga ccccctggtg    2520
gagaactttg agcctctcta tgacctggac gactcttggg agaaggctgg agaagatgag    2580
ggagtggtgc caggtaccac acccctggac atggctgcca actggcaggt atttgacata    2640
ctaaatggga aaccgtatga gcctgtgttc acatctgatg atatactacc acaaggggac    2700
atgaagcagc tgacagaaga cacgaggcta caactctgca aactgctgga aattcctgat    2760
ccagacaaaa actgggccac tctggcacag aagttgggtc tggggatatt gaacaatgcc    2820
ttccggctga gtcctgctcc ttctaaaact ctcatggaca actatgaggt ctctgggggt    2880
accatcaaag agctgatgga ggccctgcaa cagatgggct acacagaggc cattgaagtg    2940
atccaggcag cctccgcac cccggcaacc acagcctcca gccccgtgac cactgctcag    3000
gtccactgtc tgcctctctc gtcttcctcc acgaggcagc acatagatga actccgggat    3060
agtgacagcg tctgtgacag tggtgtggag acatccttcc gcaaactcag ctttacagag    3120
tctcttactg gagacagccc actgctatct ctgaacaaaa tgccccacgg ttatgggcag    3180
gaaggaccta ttgaaggcaa aatttagcct gctggccgtt ccccacact gtgtaaacca    3240 aagccctgac agtccattgc atcgtcccaa aggaggaagg caaagcgaat ccaaaggtgc    3300
tggagaatcg ccggcctgca gggtcactcg atttcattca aggccttccg aatttggcgt    3360
ccttcttggt tctgaaatga aatgtagttg ccacgcacag acggtgtcta gcaatcatgg    3420
cgctcgctcg ctcagctgca ctctatggct caggtgcagt gtcttgagct ttctctgctg    3480
ctactggatc acatttgctt tgtgttgtta ctgctgtccc tccgctgggt tcctgctgtc    3540
attaaaaggt gtcgctgtcc ccacccggtg tcctttctag ccatctactg taagttgtgc    3600
attcaaatta agattaagga aaaacatatt tttaaatgag taccttgatg cgcaataaaa    3660
aaaaagacat ttctttttt aatgtggttt atctgtgatt taaaaataaa aaacacatga    3720
acttatcaat atttaaaaca tgctacaatc agtgntgaaa atagtatttt ccccgtttta    3780
tgcattttac atttgtaaat atgttttcta atcaatactt taaagaagaa atgttgaatt    3840
tataaaatgc tatttacttt tttatttata ataaagtaca gcacatgtga ct            3892
```

<210> SEQ ID NO 2
<211> LENGTH: 971
<212> TYPE: PRT
<213> ORGANISM: Mus musculus

<400> SEQUENCE: 2

```
Met Ala Asp Asp Asp Pro Tyr Gly Thr Gly Gln Met Phe His Leu Asn
  1               5                   10                  15

Thr Ala Leu Thr His Ser Ile Phe Asn Ala Glu Leu Tyr Ser Pro Glu
             20                  25                  30

Ile Pro Leu Ser Thr Asp Gly Pro Tyr Leu Gln Ile Leu Glu Gln Pro
         35                  40                  45

Lys Gln Arg Gly Phe Arg Phe Arg Tyr Val Cys Glu Gly Pro Ser His
     50                  55                  60

Gly Gly Leu Pro Gly Ala Ser Ser Glu Lys Asn Lys Lys Ser Tyr Pro
 65                  70                  75                  80
```

```
Gln Val Lys Ile Cys Asn Tyr Val Gly Pro Ala Lys Val Ile Val Gln
                85                  90                  95
Leu Val Thr Asn Gly Lys Asn Ile His Leu His Ala His Ser Leu Val
            100                 105                 110
Gly Lys His Cys Glu Asp Gly Val Cys Thr Val Thr Ala Gly Pro Lys
        115                 120                 125
Asp Met Val Val Gly Phe Ala Asn Leu Gly Ile Leu His Val Thr Lys
    130                 135                 140
Lys Lys Val Phe Glu Thr Leu Glu Ala Arg Met Thr Glu Ala Cys Ile
145                 150                 155                 160
Arg Gly Tyr Asn Pro Gly Leu Leu Val His Ser Asp Leu Ala Tyr Leu
                165                 170                 175
Gln Ala Glu Gly Gly Gly Asp Arg Gln Leu Thr Asp Arg Glu Lys Glu
            180                 185                 190
Ile Ile Arg Gln Ala Ala Val Gln Gln Thr Lys Glu Met Asp Leu Ser
        195                 200                 205
Val Val Arg Leu Met Phe Thr Ala Phe Leu Pro Asp Ser Thr Gly Ser
    210                 215                 220
Phe Thr Arg Arg Leu Glu Pro Val Val Ser Asp Ala Ile Tyr Asp Ser
225                 230                 235                 240
Lys Ala Pro Asn Ala Ser Asn Leu Lys Ile Val Arg Met Asp Arg Thr
                245                 250                 255
Ala Gly Cys Val Thr Gly Gly Glu Ile Tyr Leu Leu Cys Asp Lys
            260                 265                 270
Val Gln Lys Asp Asp Ile Gln Ile Arg Phe Tyr Glu Glu Glu Asn
        275                 280                 285
Gly Gly Val Trp Glu Gly Phe Gly Asp Phe Ser Pro Thr Asp Val His
    290                 295                 300
Arg Gln Phe Ala Ile Val Phe Lys Thr Pro Lys Tyr Lys Asp Val Asn
305                 310                 315                 320
Ile Thr Lys Pro Ala Ser Val Phe Val Gln Leu Arg Arg Lys Ser Asp
                325                 330                 335
Leu Glu Thr Ser Glu Pro Lys Pro Phe Leu Tyr Tyr Pro Glu Ile Lys
            340                 345                 350
Asp Lys Glu Glu Val Gln Arg Lys Arg Gln Lys Leu Met Pro Asn Phe
        355                 360                 365
Ser Asp Ser Phe Gly Gly Gly Ser Gly Ala Gly Ala Gly Gly Gly Gly
    370                 375                 380
Met Phe Gly Ser Gly Gly Gly Gly Ser Thr Gly Ser Pro Gly Pro
385                 390                 395                 400
Gly Tyr Gly Tyr Ser Asn Tyr Gly Phe Pro Pro Tyr Gly Gly Ile Thr
                405                 410                 415
Phe His Pro Gly Val Thr Lys Ser Asn Ala Gly Val Thr His Gly Thr
            420                 425                 430
Ile Asn Thr Lys Phe Lys Asn Gly Pro Lys Asp Cys Ala Lys Ser Asp
        435                 440                 445
Asp Glu Glu Ser Leu Thr Leu Pro Glu Lys Glu Thr Glu Gly Glu Gly
    450                 455                 460
Pro Ser Leu Pro Met Ala Cys Thr Lys Thr Glu Pro Ile Ala Leu Ala
465                 470                 475                 480
Ser Thr Met Glu Asp Lys Glu Gln Asp Met Gly Phe Gln Asp Asn Leu
                485                 490                 495
Phe Leu Glu Lys Ala Leu Gln Leu Ala Arg Arg His Ala Asn Ala Leu
```

```
                500             505             510
Phe Asp Tyr Ala Val Thr Gly Asp Val Lys Met Leu Leu Ala Val Gln
        515                 520                 525
Arg His Leu Thr Ala Val Gln Asp Glu Asn Gly Asp Ser Val Leu His
        530                 535                 540
Leu Ala Ile Ile His Leu His Ala Gln Leu Val Arg Asp Leu Leu Glu
545                 550                 555                 560
Val Thr Ser Gly Leu Ile Ser Asp Asp Ile Ile Asn Met Arg Asn Asp
                565                 570                 575
Leu Tyr Gln Thr Pro Leu His Leu Ala Val Ile Thr Lys Gln Glu Asp
            580                 585                 590
Val Val Glu Asp Leu Leu Arg Val Gly Ala Asp Leu Ser Leu Leu Asp
            595                 600                 605
Arg Trp Gly Asn Ser Val Leu His Leu Ala Ala Lys Glu Gly His Asp
            610                 615                 620
Arg Ile Leu Ser Ile Leu Leu Lys Ser Arg Lys Ala Ala Pro Leu Ile
625                 630                 635                 640
Asp His Pro Asn Gly Glu Gly Leu Asn Ala Ile His Ile Ala Val Met
                645                 650                 655
Ser Asn Ser Leu Pro Cys Leu Leu Leu Leu Val Ala Ala Gly Ala Glu
            660                 665                 670
Val Asn Ala Gln Glu Gln Lys Ser Gly Arg Thr Pro Leu His Leu Ala
            675                 680                 685
Val Glu Tyr Asp Asn Ile Ser Leu Ala Gly Cys Leu Leu Leu Glu Gly
            690                 695                 700
Asp Ala His Val Asp Ser Thr Thr Tyr Asp Gly Thr Thr Pro Leu His
705                 710                 715                 720
Ile Ala Ala Gly Arg Gly Ser Thr Arg Leu Ala Ala Leu Leu Lys Ala
                725                 730                 735
Ala Gly Ala Asp Pro Leu Val Glu Asn Phe Glu Pro Leu Tyr Asp Leu
            740                 745                 750
Asp Asp Ser Trp Glu Lys Ala Gly Glu Asp Glu Gly Val Val Pro Gly
            755                 760                 765
Thr Thr Pro Leu Asp Met Ala Ala Asn Trp Gln Val Phe Asp Ile Leu
770                 775                 780
Asn Gly Lys Pro Tyr Glu Pro Val Phe Thr Ser Asp Asp Ile Leu Pro
785                 790                 795                 800
Gln Gly Asp Met Lys Gln Leu Thr Glu Asp Thr Arg Leu Gln Leu Cys
                805                 810                 815
Lys Leu Leu Glu Ile Pro Asp Pro Asp Lys Asn Trp Ala Thr Leu Ala
            820                 825                 830
Gln Lys Leu Gly Leu Gly Ile Leu Asn Asn Ala Phe Arg Leu Ser Pro
            835                 840                 845
Ala Pro Ser Lys Thr Leu Met Asp Asn Tyr Glu Val Ser Gly Gly Thr
            850                 855                 860
Ile Lys Glu Leu Met Glu Ala Leu Gln Gln Met Gly Tyr Thr Glu Ala
865                 870                 875                 880
Ile Glu Val Ile Gln Ala Ala Phe Arg Thr Pro Ala Thr Thr Ala Ser
                885                 890                 895
Ser Pro Val Thr Thr Ala Gln Val His Cys Leu Pro Leu Ser Ser Ser
            900                 905                 910
Ser Thr Arg Gln His Ile Asp Glu Leu Arg Asp Ser Asp Ser Val Cys
            915                 920                 925
```

```
Asp Ser Gly Val Glu Thr Ser Phe Arg Lys Leu Ser Phe Thr Glu Ser
            930                 935                 940

Leu Thr Gly Asp Ser Pro Leu Leu Ser Leu Asn Lys Met Pro His Gly
945                 950                 955                 960

Tyr Gly Gln Glu Gly Pro Ile Glu Gly Lys Ile
                965                 970

<210> SEQ ID NO 3
<211> LENGTH: 3205
<212> TYPE: DNA
<213> ORGANISM: Homo sapiens

<400> SEQUENCE: 3
```

| | | | | | |
|---|---|---|---|---|---|
| ggaattccct | ggcctggccc | ggccccgccg | cgctcccgct | cgccccgacc | cgcactcggg | 60 |
| cccgcccggg | ctccggcctg | ccgccgcctc | ttccttctcc | agccggcagg | cccgcgccgc | 120 |
| ttaggaggga | gagcccaccc | gcgccaggag | gccgaacgcg | gactcgccac | ccggcttcag | 180 |
| aatggcagaa | gatgatccat | atttgggaag | gcctgaacaa | atgtttcatt | tggatccttc | 240 |
| tttgactcat | acaatattta | atccagaagt | atttcaacca | cagatggcac | tgccaacagc | 300 |
| agatggccca | taccttcaaa | tattagcaca | acctaaacag | agaggatttc | gtttccgtta | 360 |
| tgtatgtgaa | ggcccatccc | atggtggact | acctggtgcc | tctagtgaaa | agaacaagaa | 420 |
| gtcttaccct | caggtcaaaa | tctgcaacta | tgtgggacca | gcaaaggtta | ttgttcagtt | 480 |
| ggtcacaaat | ggaaaaaata | tccacctgca | tgcccacagc | ctggtgggaa | acactgtga | 540 |
| ggatgggatc | tgcactgtaa | ctgctggacc | caaggacatg | gtggtcggct | cgcaaacct | 600 |
| gggtatactt | catgtgacaa | agaaaaaagt | atttgaaaca | ctggaagcac | gaatgacaga | 660 |
| ggcgtgtata | aggggctata | atcctggact | cttggtgcac | cctgaccttg | cctatttgca | 720 |
| agcagaaggt | ggaggggacc | ggcagctggg | agatcgggaa | aaagagctaa | tccgccaagc | 780 |
| agctctgcag | cagaccaagg | agatggacct | cagcgtggtg | cggctcatgt | ttacagcttt | 840 |
| tcttccggat | agcactggca | gcttcacaag | gcgcctggaa | cccgtggtat | cagacgccat | 900 |
| ctatgacagt | aaagccccca | atgcatccaa | cttgaaaatt | gtaagaatgg | acaggacagc | 960 |
| tggatgtgtg | actggagggg | aggaaattta | tcttctttgt | gacaaagttc | agaaagatga | 1020 |
| catccagatt | cgatttatg | aagaggaaga | aaatggtgga | gtctgggaag | gatttggaga | 1080 |
| ttttttcccc | acagatgttc | atagacaatt | tgccattgtc | ttcaaaactc | caaagtataa | 1140 |
| agatattaat | attacaaaac | cagcctctgt | gtttgtccag | cttcggagga | atctgacttt | 1200 |
| ggaaactagt | gaaccaaaac | ctttcctcta | ctatcctgaa | atcaaagata | agaagaagagt | 1260 |
| gcagaggaaa | cgtcagaagc | tcatgcccaa | tttttcggat | agtttcggcg | gtggtagtgg | 1320 |
| tgccggagct | ggaggcggag | gcatgtttgg | tagtggcggt | ggaggagggg | gcactggaag | 1380 |
| tacaggtcca | gggtatagct | tcccacacta | tggatttcct | acttatgtg | ggattacttt | 1440 |
| ccatcctgga | actactaaat | ctaatgctgg | gatgaagcat | ggaaccatgg | acactgaatc | 1500 |
| taaaaaggac | cctgaaggtt | gtgacaaaag | tgatgacaaa | aacactgtaa | acctctttgg | 1560 |
| gaaagttatt | gaaccacag | agcaagatca | ggagcccagc | gaggccaccg | ttgggaatgg | 1620 |
| tgaggtcact | ctaacgtatg | caacaggaac | aaaagaagag | agtgctggag | ttcaggataa | 1680 |
| cctcttttcta | gagaaggcta | tgcagcttgc | aaagaggcat | gccaatgccc | ttttcgacta | 1740 |
| cgcggtgaca | ggagacgtga | agatgctgct | ggccgtccag | cgccatctca | ctgctgtgca | 1800 |
| ggatgagaat | ggggacagtg | tcttacactt | agcaatcatc | caccttcatt | ctcaacttgt | 1860 |
| gagggatcta | ctagaagtca | catctggttt | gatttctgat | gacattatca | acatgagaaa | 1920 |

```
tgatctgtac cagacgccct tgcacttggc agtgatcact aagcaggaag atgtggtgga    1980
ggatttgctg agggctgggg ccgacctgag ccttctggac cgcttgggta actctgtttt    2040
gcacctagct gccaaagaag gacatgataa agttctcagt atcttactca agcacaaaaa    2100
ggcagcacta cttcttgacc accccaacgg ggacggtctg aatgccattc atctagccat    2160
gatgagcaat agcctgccat gtttgctgct gctggtggcc gctggggctg acgtcaatgc    2220
tcaggagcag aagtccgggc gcacagcact gcacctggct gtggagcacg acaacatctc    2280
attggcaggc tgcctgctcc tggagggtga tgcccatgtg acagtactac cctacgatgg    2340
aaccacaccc ctgcatatag cagctgggag agggtccacc aggctggcag ctcttctcaa    2400
agcagcagga gcagatcccc tggtggagaa ctttgagcct ctctatgacc tggatgactc    2460
ttgggaaaat gcaggagagg atgaaggagt tgtgcctgga accacgcctc tagatatggc    2520
caccagctgg caggtatttg acatattaaa tgggaaacca tatgagccag agtttacatc    2580
tgatgattta ctagcacaag gagacatgaa acagctggct gaagatgtga agctgcagct    2640
gtataagtta ctagaaattc ctgatccaga caaaaactgg gctactctgg cgcagaaatt    2700
aggtctgggg atacttaata atgccttccg gctgagtcct gctccttcca aaacacttat    2760
ggacaactat gaggtctctg ggggtacagt cagagagctg gtggaggccc tgagacaaat    2820
gggctacacc gaagcaattg aagtgatcca ggcagcctcc agcccagtga agaccacctc    2880
tcaggcccac tcgctgcctc tctcgcctgc ctccacaagg cagcaaatag cgagctccg    2940 agacagtgac agtgtctgcg cacgggcgt ggagacatcc ttccgcaaac tcagctttac    3000
cgagtctctg accagtggtg cctcactgct aactctcaac aaaatgcccc atgattatgg    3060
gcaggaagga cctctagaag gcaaaattta gcctgctgac aatttcccac accgtgtaaa    3120
ccaaagccct aaaattcact gcgttgtcca aagacagaa gctgaagtgc atcccaaagg    3180
tgctcagaga gccggccgga attcc    3205
```

<210> SEQ ID NO 4
<211> LENGTH: 969
<212> TYPE: PRT
<213> ORGANISM: Homo sapiens

<400> SEQUENCE: 4

```
Met Ala Glu Asp Asp Pro Tyr Leu Gly Arg Pro Glu Gln Met Phe His
  1               5                  10                  15

Leu Asp Pro Ser Leu Thr His Thr Ile Phe Asn Pro Glu Val Phe Gln
             20                  25                  30

Pro Gln Met Ala Leu Pro Thr Ala Asp Gly Pro Tyr Leu Gln Ile Leu
         35                  40                  45

Glu Gln Pro Lys Gln Arg Gly Phe Arg Phe Arg Tyr Val Cys Glu Gly
     50                  55                  60

Pro Ser His Gly Gly Leu Pro Gly Ala Ser Ser Glu Lys Asn Lys Lys
 65                  70                  75                  80

Ser Tyr Pro Gln Val Lys Ile Cys Asn Tyr Val Gly Pro Ala Lys Val
                 85                  90                  95

Ile Val Gln Leu Val Thr Asn Gly Lys Asn Ile His Leu His Ala His
            100                 105                 110

Ser Leu Val Gly Lys His Cys Glu Asp Gly Ile Cys Thr Val Thr Ala
        115                 120                 125

Gly Pro Lys Asp Met Val Val Gly Phe Ala Asn Leu Gly Ile Leu His
    130                 135                 140
```

-continued

```
Val Thr Lys Lys Lys Val Phe Glu Thr Leu Glu Ala Arg Met Thr Glu
145                 150                 155                 160

Ala Cys Ile Arg Gly Tyr Asn Pro Gly Leu Val His Pro Asp Leu
            165                 170                 175

Ala Tyr Leu Gln Ala Glu Gly Gly Asp Arg Gln Leu Gly Asp Arg
        180                 185                 190

Glu Lys Glu Leu Ile Arg Gln Ala Ala Leu Gln Gln Thr Lys Glu Met
            195                 200                 205

Asp Leu Ser Val Val Arg Leu Met Phe Thr Ala Phe Leu Pro Asp Ser
    210                 215                 220

Thr Gly Ser Phe Thr Arg Arg Leu Glu Pro Val Val Ser Asp Ala Ile
225                 230                 235                 240

Tyr Asp Ser Lys Ala Pro Asn Ala Ser Asn Leu Lys Ile Val Arg Met
            245                 250                 255

Asp Arg Thr Ala Gly Cys Val Thr Gly Gly Glu Glu Ile Tyr Leu Leu
            260                 265                 270

Cys Asp Lys Val Gln Lys Asp Ile Gln Ile Arg Phe Tyr Glu Glu
        275                 280                 285

Glu Glu Asn Gly Gly Val Trp Glu Gly Phe Gly Asp Phe Ser Pro Thr
    290                 295                 300

Asp Val His Arg Gln Phe Ala Ile Val Phe Lys Thr Pro Lys Tyr Lys
305                 310                 315                 320

Asp Ile Asn Ile Thr Lys Pro Ala Ser Val Phe Val Gln Leu Arg Arg
            325                 330                 335

Lys Ser Asp Leu Glu Thr Ser Glu Pro Lys Pro Phe Leu Tyr Tyr Pro
            340                 345                 350

Glu Ile Lys Asp Lys Glu Glu Val Gln Arg Lys Arg Gln Lys Leu Met
            355                 360                 365

Pro Asn Phe Ser Asp Ser Phe Gly Gly Gly Ser Gly Ala Gly Ala Gly
    370                 375                 380

Gly Gly Gly Met Phe Gly Ser Gly Gly Gly Gly Gly Thr Gly Ser
385                 390                 395                 400

Thr Gly Pro Gly Tyr Ser Phe Pro His Tyr Gly Phe Pro Thr Tyr Gly
            405                 410                 415

Gly Ile Thr Phe His Pro Gly Thr Thr Lys Ser Asn Ala Gly Met Lys
            420                 425                 430

His Gly Thr Met Asp Thr Glu Ser Lys Lys Asp Pro Glu Gly Cys Asp
            435                 440                 445

Lys Ser Asp Asp Lys Asn Thr Val Asn Leu Phe Gly Lys Val Ile Glu
    450                 455                 460

Thr Thr Glu Gln Asp Gln Glu Pro Ser Glu Ala Thr Val Gly Asn Gly
465                 470                 475                 480

Glu Val Thr Leu Thr Tyr Ala Thr Gly Thr Lys Glu Glu Ser Ala Gly
            485                 490                 495

Val Gln Asp Asn Leu Phe Leu Glu Lys Ala Met Gln Leu Ala Lys Arg
        500                 505                 510

His Ala Asn Ala Leu Phe Asp Tyr Ala Val Thr Gly Asp Val Lys Met
            515                 520                 525

Leu Leu Ala Val Gln Arg His Leu Thr Ala Val Gln Asp Glu Asn Gly
    530                 535                 540

Asp Ser Val Leu His Leu Ala Ile Ile His Leu His Ser Gln Leu Val
545                 550                 555                 560

Arg Asp Leu Leu Glu Val Thr Ser Gly Leu Ile Ser Asp Asp Ile Ile
            565                 570                 575
```

```
Asn Met Arg Asn Asp Leu Tyr Gln Thr Pro Leu His Leu Ala Val Ile
            580                 585                 590

Thr Lys Gln Glu Asp Val Val Glu Asp Leu Leu Arg Ala Gly Ala Asp
        595                 600                 605

Leu Ser Leu Leu Asp Arg Leu Gly Asn Ser Val Leu His Leu Ala Ala
610                 615                 620

Lys Glu Gly His Asp Lys Val Leu Ser Ile Leu Leu Lys His Lys Lys
625                 630                 635                 640

Ala Ala Leu Leu Leu Asp His Pro Asn Gly Asp Gly Leu Asn Ala Ile
            645                 650                 655

His Leu Ala Met Met Ser Asn Ser Leu Pro Cys Leu Leu Leu Leu Val
            660                 665                 670

Ala Ala Gly Ala Asp Val Asn Ala Gln Glu Gln Lys Ser Gly Arg Thr
        675                 680                 685

Ala Leu His Leu Ala Val Glu His Asp Asn Ile Ser Leu Ala Gly Cys
        690                 695                 700

Leu Leu Leu Glu Gly Asp Ala His Val Asp Ser Thr Thr Tyr Asp Gly
705                 710                 715                 720

Thr Thr Pro Leu His Ile Ala Ala Gly Arg Gly Ser Thr Arg Leu Ala
            725                 730                 735

Ala Leu Leu Lys Ala Ala Gly Ala Asp Pro Leu Val Glu Asn Phe Glu
            740                 745                 750

Pro Leu Tyr Asp Leu Asp Asp Ser Trp Glu Asn Ala Gly Glu Asp Glu
        755                 760                 765

Gly Val Val Pro Gly Thr Thr Pro Leu Asp Met Ala Thr Ser Trp Gln
770                 775                 780

Val Phe Asp Ile Leu Asn Gly Lys Pro Tyr Pro Glu Phe Thr Ser
785                 790                 795                 800

Asp Asp Leu Leu Ala Gln Gly Asp Met Lys Gln Leu Ala Glu Asp Val
            805                 810                 815

Lys Leu Gln Leu Tyr Lys Leu Leu Glu Ile Pro Asp Pro Asp Lys Asn
            820                 825                 830

Trp Ala Thr Leu Ala Gln Lys Leu Gly Leu Gly Ile Leu Asn Asn Ala
        835                 840                 845

Phe Arg Leu Ser Pro Ala Pro Ser Lys Thr Leu Met Asp Asn Tyr Glu
        850                 855                 860

Val Ser Gly Gly Thr Val Arg Glu Leu Val Glu Ala Leu Arg Gln Met
865                 870                 875                 880

Gly Tyr Thr Glu Ala Ile Glu Val Ile Gln Ala Ala Ser Ser Pro Val
            885                 890                 895

Lys Thr Thr Ser Gln Ala His Ser Leu Pro Leu Ser Pro Ala Ser Thr
            900                 905                 910

Arg Gln Gln Ile Asp Glu Leu Arg Asp Ser Asp Ser Val Cys Asp Thr
        915                 920                 925

Gly Val Glu Thr Ser Phe Arg Lys Leu Ser Phe Thr Glu Ser Leu Thr
        930                 935                 940

Ser Gly Ala Ser Leu Leu Thr Leu Asn Lys Met Pro His Asp Tyr Gly
945                 950                 955                 960

Gln Glu Gly Pro Leu Glu Gly Lys Ile
            965

<210> SEQ ID NO 5
<211> LENGTH: 2034
<212> TYPE: DNA
```

<213> ORGANISM: Mus musculus
<220> FEATURE:
<221> NAME/KEY: CDS
<222> LOCATION: (1)..(2031)

<400> SEQUENCE: 5

```
atg gct agc atg act ggt gga cag caa atg ggt act gga tcc atg gca      48
Met Ala Ser Met Thr Gly Gly Gln Gln Met Gly Thr Gly Ser Met Ala
1               5                   10                  15 gac gat gat ccc tac gga act ggg caa atg ttt cat ttg aac act gct      96
Asp Asp Asp Pro Tyr Gly Thr Gly Gln Met Phe His Leu Asn Thr Ala
                20                  25                  30 ttg act cac tca ata ttt aat gca gaa tta tat tca cca gaa ata cca     144
Leu Thr His Ser Ile Phe Asn Ala Glu Leu Tyr Ser Pro Glu Ile Pro
            35                  40                  45 ctg tca aca gat ggc cca tac ctt caa ata tta gag caa cca aaa cag     192
Leu Ser Thr Asp Gly Pro Tyr Leu Gln Ile Leu Glu Gln Pro Lys Gln
50                  55                  60 agg gga ttt cga ttc cgc tat gtg tgt gaa ggc cca tca cac gga ggg     240
Arg Gly Phe Arg Phe Arg Tyr Val Cys Glu Gly Pro Ser His Gly Gly
65                  70                  75                  80 ctt ccg gga gcc tct agt gag aag aac aag aaa tcc tac cca cag gtc     288
Leu Pro Gly Ala Ser Ser Glu Lys Asn Lys Lys Ser Tyr Pro Gln Val
                85                  90                  95 aaa att tgc aac tat gtg ggg cct gca aag gtt atc gtt cag ttg gtc     336
Lys Ile Cys Asn Tyr Val Gly Pro Ala Lys Val Ile Val Gln Leu Val
                100                 105                 110 aca aat gga aaa aac atc cac ctg cac gcc cac agc ctg gtg ggc aag     384
Thr Asn Gly Lys Asn Ile His Leu His Ala His Ser Leu Val Gly Lys
            115                 120                 125 cac tgt gag gac ggg gta tgc acc gta aca gca gga ccc aag gac atg     432
His Cys Glu Asp Gly Val Cys Thr Val Thr Ala Gly Pro Lys Asp Met
130                 135                 140 gtg gtt ggc ttt gca aac ctg gga ata ctt cat gtg act aag aaa aag     480
Val Val Gly Phe Ala Asn Leu Gly Ile Leu His Val Thr Lys Lys Lys
145                 150                 155                 160 gta ttt gaa aca ctg gaa gca cgg atg aca gag gcg tgt att agg ggc     528
Val Phe Glu Thr Leu Glu Ala Arg Met Thr Glu Ala Cys Ile Arg Gly
                165                 170                 175 tat aat cct gga ctt ctg gtg cat tct gac ctt gcc tat cta caa gca     576
Tyr Asn Pro Gly Leu Leu Val His Ser Asp Leu Ala Tyr Leu Gln Ala
            180                 185                 190 gaa ggc gga gga gac cgg caa ctc aca gac aga gag aag gag atc atc     624
Glu Gly Gly Gly Asp Arg Gln Leu Thr Asp Arg Glu Lys Glu Ile Ile
        195                 200                 205 cgc cag gca gcc gtg cag cag acc aag gag atg gac ctg agc gtg gtg     672
Arg Gln Ala Ala Val Gln Gln Thr Lys Glu Met Asp Leu Ser Val Val
210                 215                 220 cgc ctc atg ttc aca gcc ttc ctc cct gac agc act ggc agc ttc act     720
Arg Leu Met Phe Thr Ala Phe Leu Pro Asp Ser Thr Gly Ser Phe Thr
225                 230                 235                 240 cgg aga ctg gag cct gtg gtg tca gac gcc atc tat gat agc aaa gcc     768
Arg Arg Leu Glu Pro Val Val Ser Asp Ala Ile Tyr Asp Ser Lys Ala
                245                 250                 255 ccg aat gca tcc aac ctg aaa atc gtg aga atg gac aga aca gca gga     816
Pro Asn Ala Ser Asn Leu Lys Ile Val Arg Met Asp Arg Thr Ala Gly
            260                 265                 270 tgt gtg acg gga ggg gag gag att tac ctt ctc tgt gac aag gtt cag     864
Cys Val Thr Gly Gly Glu Glu Ile Tyr Leu Leu Cys Asp Lys Val Gln
        275                 280                 285 aaa gat gac atc cag att cgg ttt tat gaa gag gaa gaa aat ggc gga     912
Lys Asp Asp Ile Gln Ile Arg Phe Tyr Glu Glu Glu Glu Asn Gly Gly
```

```
                    -continued

Lys Asp Asp Ile Gln Ile Arg Phe Tyr Glu Glu Glu Asn Gly Gly
    290                 295                 300 gtt tgg gaa gga ttt ggg gac ttt tcc ccc acg gat gtt cat aga cag    960
Val Trp Glu Gly Phe Gly Asp Phe Ser Pro Thr Asp Val His Arg Gln
305                 310                 315                 320 ttt gcc att gtc ttc aaa acg cca aag tat aag gat gtc aac att aca   1008
Phe Ala Ile Val Phe Lys Thr Pro Lys Tyr Lys Asp Val Asn Ile Thr
                325                 330                 335 aag cca gct tcc gtg ttt gtt cag ctt cgg agg aaa tca gac ctg gaa   1056
Lys Pro Ala Ser Val Phe Val Gln Leu Arg Arg Lys Ser Asp Leu Glu
            340                 345                 350 act agt gaa ccg aaa ccc ttt ctc tac tac cct gaa atc aaa gac aaa   1104
Thr Ser Glu Pro Lys Pro Phe Leu Tyr Tyr Pro Glu Ile Lys Asp Lys
        355                 360                 365 gag gaa aag ctg act agt aag gct ctg cag ctc gcc agg cga cac gcc   1152
Glu Glu Lys Leu Thr Ser Lys Ala Leu Gln Leu Ala Arg Arg His Ala
    370                 375                 380 aac gcc ctt ttc gac tac gca gtg acg ggg gat gtg aag atg ttg ctg   1200
Asn Ala Leu Phe Asp Tyr Ala Val Thr Gly Asp Val Lys Met Leu Leu
385                 390                 395                 400 gcc gtg caa cgc cat ctc acc gcc gtg cag gat gag aat ggg gac agt   1248
Ala Val Gln Arg His Leu Thr Ala Val Gln Asp Glu Asn Gly Asp Ser
                405                 410                 415 gtc tta cac tta gcc atc atc cac ctc cac gct cag ctc gtg agg gat   1296
Val Leu His Leu Ala Ile Ile His Leu His Ala Gln Leu Val Arg Asp
            420                 425                 430 ctg ctg gaa gtc aca tct ggt ttg atc tct gat gac atc atc aac atg   1344
Leu Leu Glu Val Thr Ser Gly Leu Ile Ser Asp Asp Ile Ile Asn Met
        435                 440                 445 aga aat gac ctg tat cag aca cct ctg cac ttg gcc gtg atc acc aag   1392
Arg Asn Asp Leu Tyr Gln Thr Pro Leu His Leu Ala Val Ile Thr Lys
    450                 455                 460 cag gaa gat gta gta gag gat ttg ctg agg gtt ggg gct gac ctg agc   1440
Gln Glu Asp Val Val Glu Asp Leu Leu Arg Val Gly Ala Asp Leu Ser
465                 470                 475                 480 ctt ctg gac cgc tgg ggc aac tct gtc ctg cac cta gct gcc aaa gaa   1488
Leu Leu Asp Arg Trp Gly Asn Ser Val Leu His Leu Ala Ala Lys Glu
                485                 490                 495 gga cac gac aga atc ctc agc atc ctg ctc aag agc aga aaa gca gcg   1536
Gly His Asp Arg Ile Leu Ser Ile Leu Leu Lys Ser Arg Lys Ala Ala
            500                 505                 510 ccc ctt atc gac cac ccc aat ggg gaa ggt cta aat gcc atc cac ata   1584
Pro Leu Ile Asp His Pro Asn Gly Glu Gly Leu Asn Ala Ile His Ile
        515                 520                 525 gct gtg atg agc aat agc ctg cca tgt ctg ctg ctg gtg gct gcc      1632
Ala Val Met Ser Asn Ser Leu Pro Cys Leu Leu Leu Val Ala Ala
    530                 535                 540 ggg gca gaa gtc aat gct cag gag cag aag tct ggg cgc acg ccg ctg   1680
Gly Ala Glu Val Asn Ala Gln Glu Gln Lys Ser Gly Arg Thr Pro Leu
545                 550                 555                 560 cac ctg gcc gtg gag tac gac aac atc tcc ttg gct ggc tgc ctg ctt   1728
His Leu Ala Val Glu Tyr Asp Asn Ile Ser Leu Ala Gly Cys Leu Leu
                565                 570                 575 ctg gag ggt gat gcc cac gtg gac agt acc acc tat gat ggg act aca   1776
Leu Glu Gly Asp Ala His Val Asp Ser Thr Thr Tyr Asp Gly Thr Thr
            580                 585                 590 cct ctg cat ata gcg gcc gga aga ggg tcc acc aga ctg gca gct ctt   1824
Pro Leu His Ile Ala Ala Gly Arg Gly Ser Thr Arg Leu Ala Ala Leu
        595                 600                 605 ctc aaa gca gca gga gca gac ccc ctg gtg gag aac ttt gag cct ctc   1872
```

```
Leu Lys Ala Ala Gly Ala Asp Pro Leu Val Glu Asn Phe Glu Pro Leu
        610                 615                 620 tat gac ctg gac gac tct tgg gag aag gct gga gaa gat gag gga gtg      1920
Tyr Asp Leu Asp Asp Ser Trp Glu Lys Ala Gly Glu Asp Glu Gly Val
625                 630                 635                 640 gtg cca ggt acc aca ccc ctg gac atg gct gcc aac tgg cag gta ttt      1968
Val Pro Gly Thr Thr Pro Leu Asp Met Ala Ala Asn Trp Gln Val Phe
                645                 650                 655 gac ata cta aat ggg aaa ccg tat gag cct gtg ttc aca tct gat gat      2016
Asp Ile Leu Asn Gly Lys Pro Tyr Glu Pro Val Phe Thr Ser Asp Asp
            660                 665                 670 ata cta cca gga tcc tag                                              2034
Ile Leu Pro Gly Ser
            675

<210> SEQ ID NO 6
<211> LENGTH: 677
<212> TYPE: PRT
<213> ORGANISM: Mus musculus

<400> SEQUENCE: 6

Met Ala Ser Met Thr Gly Gly Gln Gln Met Gly Thr Gly Ser Met Ala
1               5                   10                  15

Asp Asp Asp Pro Tyr Gly Thr Gly Gln Met Phe His Leu Asn Thr Ala
            20                  25                  30

Leu Thr His Ser Ile Phe Asn Ala Glu Leu Tyr Ser Pro Glu Ile Pro
        35                  40                  45

Leu Ser Thr Asp Gly Pro Tyr Leu Gln Ile Leu Glu Gln Pro Lys Gln
    50                  55                  60

Arg Gly Phe Arg Phe Arg Tyr Val Cys Glu Gly Pro Ser His Gly Gly
65                  70                  75                  80

Leu Pro Gly Ala Ser Ser Glu Lys Asn Lys Lys Ser Tyr Pro Gln Val
                85                  90                  95

Lys Ile Cys Asn Tyr Val Gly Pro Ala Lys Val Ile Val Gln Leu Val
            100                 105                 110

Thr Asn Gly Lys Asn Ile His Leu His Ala His Ser Leu Val Gly Lys
        115                 120                 125

His Cys Glu Asp Gly Val Cys Thr Val Thr Ala Gly Pro Lys Asp Met
    130                 135                 140

Val Val Gly Phe Ala Asn Leu Gly Ile Leu His Val Thr Lys Lys Lys
145                 150                 155                 160

Val Phe Glu Thr Leu Glu Ala Arg Met Thr Glu Ala Cys Ile Arg Gly
                165                 170                 175

Tyr Asn Pro Gly Leu Leu Val His Ser Asp Leu Ala Tyr Leu Gln Ala
            180                 185                 190

Glu Gly Gly Gly Asp Arg Gln Leu Thr Asp Arg Glu Lys Glu Ile Ile
        195                 200                 205

Arg Gln Ala Ala Val Gln Gln Thr Lys Glu Met Asp Leu Ser Val Val
    210                 215                 220

Arg Leu Met Phe Thr Ala Phe Leu Pro Asp Ser Thr Gly Ser Phe Thr
225                 230                 235                 240

Arg Arg Leu Glu Pro Val Val Ser Asp Ala Ile Tyr Asp Ser Lys Ala
                245                 250                 255

Pro Asn Ala Ser Asn Leu Lys Ile Val Arg Met Asp Arg Thr Ala Gly
            260                 265                 270

Cys Val Thr Gly Gly Glu Glu Ile Tyr Leu Leu Cys Asp Lys Val Gln
        275                 280                 285
```

-continued

Lys Asp Asp Ile Gln Ile Arg Phe Tyr Glu Glu Glu Asn Gly Gly
    290                 295                 300

Val Trp Glu Gly Phe Gly Asp Phe Ser Pro Thr Asp Val His Arg Gln
305                 310                 315                 320

Phe Ala Ile Val Phe Lys Thr Pro Lys Tyr Lys Asp Val Asn Ile Thr
                325                 330                 335

Lys Pro Ala Ser Val Phe Val Gln Leu Arg Arg Lys Ser Asp Leu Glu
            340                 345                 350

Thr Ser Glu Pro Lys Pro Phe Leu Tyr Tyr Pro Glu Ile Lys Asp Lys
        355                 360                 365

Glu Glu Lys Leu Thr Ser Lys Ala Leu Gln Leu Ala Arg Arg His Ala
    370                 375                 380

Asn Ala Leu Phe Asp Tyr Ala Val Thr Gly Asp Val Lys Met Leu Leu
385                 390                 395                 400

Ala Val Gln Arg His Leu Thr Ala Val Gln Asp Glu Asn Gly Asp Ser
                405                 410                 415

Val Leu His Leu Ala Ile Ile His Leu His Ala Gln Leu Val Arg Asp
            420                 425                 430

Leu Leu Glu Val Thr Ser Gly Leu Ile Ser Asp Asp Ile Ile Asn Met
        435                 440                 445

Arg Asn Asp Leu Tyr Gln Thr Pro Leu His Leu Ala Val Ile Thr Lys
    450                 455                 460

Gln Glu Asp Val Val Glu Asp Leu Leu Arg Val Gly Ala Asp Leu Ser
465                 470                 475                 480

Leu Leu Asp Arg Trp Gly Asn Ser Val Leu His Leu Ala Ala Lys Glu
                485                 490                 495

Gly His Asp Arg Ile Leu Ser Ile Leu Leu Lys Ser Arg Lys Ala Ala
            500                 505                 510

Pro Leu Ile Asp His Pro Asn Gly Glu Gly Leu Asn Ala Ile His Ile
        515                 520                 525

Ala Val Met Ser Asn Ser Leu Pro Cys Leu Leu Leu Val Ala Ala
    530                 535                 540

Gly Ala Glu Val Asn Ala Gln Glu Gln Lys Ser Gly Arg Thr Pro Leu
545                 550                 555                 560

His Leu Ala Val Glu Tyr Asp Asn Ile Ser Leu Ala Gly Cys Leu Leu
                565                 570                 575

Leu Glu Gly Asp Ala His Val Asp Ser Thr Thr Tyr Asp Gly Thr Thr
            580                 585                 590

Pro Leu His Ile Ala Ala Gly Arg Gly Ser Thr Arg Leu Ala Ala Leu
        595                 600                 605

Leu Lys Ala Ala Gly Ala Asp Pro Leu Val Glu Asn Phe Glu Pro Leu
    610                 615                 620

Tyr Asp Leu Asp Asp Ser Trp Glu Lys Ala Gly Glu Asp Glu Gly Val
625                 630                 635                 640

Val Pro Gly Thr Thr Pro Leu Asp Met Ala Ala Asn Trp Gln Val Phe
                645                 650                 655

Asp Ile Leu Asn Gly Lys Pro Tyr Glu Pro Val Phe Thr Ser Asp Asp
            660                 665                 670

Ile Leu Pro Gly Ser
            675

<210> SEQ ID NO 7
<211> LENGTH: 2052
<212> TYPE: DNA

<213> ORGANISM: Mus musculus
<220> FEATURE:
<221> NAME/KEY: CDS
<222> LOCATION: (1)..(2049)

<400> SEQUENCE: 7

```
atg gct agc atg act ggt gga cag caa atg ggt act gga tcc atg gca         48
Met Ala Ser Met Thr Gly Gly Gln Gln Met Gly Thr Gly Ser Met Ala
 1               5                  10                  15 gac gat gat ccc tac gga act ggg caa atg ttt cat ttg aac act gct         96
Asp Asp Asp Pro Tyr Gly Thr Gly Gln Met Phe His Leu Asn Thr Ala
             20                  25                  30 ttg act cac tca ata ttt aat gca gaa tta tat tca cca gaa ata cca        144
Leu Thr His Ser Ile Phe Asn Ala Glu Leu Tyr Ser Pro Glu Ile Pro
         35                  40                  45 ctg tca aca gat ggc cca tac ctt caa ata tta gag caa cca aaa cag        192
Leu Ser Thr Asp Gly Pro Tyr Leu Gln Ile Leu Glu Gln Pro Lys Gln
     50                  55                  60 agg gga ttt cga ttc cgc tat gtg tgt gaa ggc cca tca cac gga ggg        240
Arg Gly Phe Arg Phe Arg Tyr Val Cys Glu Gly Pro Ser His Gly Gly
 65                  70                  75                  80 ctt ccg gga gcc tct agt gag aag aac aag aaa tcc tac cca cag gtc        288
Leu Pro Gly Ala Ser Ser Glu Lys Asn Lys Lys Ser Tyr Pro Gln Val
                 85                  90                  95 aaa att tgc aac tat gtg ggg cct gca aag gtt atc gtt cag ttg gtc        336
Lys Ile Cys Asn Tyr Val Gly Pro Ala Lys Val Ile Val Gln Leu Val
            100                 105                 110 aca aat gga aaa aac atc cac ctg cac gcc cac agc ctg gtg ggc aag        384
Thr Asn Gly Lys Asn Ile His Leu His Ala His Ser Leu Val Gly Lys
        115                 120                 125 cac tgt gag gac ggg gta tgc acc gta aca gca gga ccc aag gac atg        432
His Cys Glu Asp Gly Val Cys Thr Val Thr Ala Gly Pro Lys Asp Met
    130                 135                 140 gtg gtt ggc ttt gca aac ctg gga ata ctt cat gtg act aag aaa aag        480
Val Val Gly Phe Ala Asn Leu Gly Ile Leu His Val Thr Lys Lys Lys
145                 150                 155                 160 gta ttt gaa aca ctg gaa gca cgg atg aca gag gcg tgt att agg ggc        528
Val Phe Glu Thr Leu Glu Ala Arg Met Thr Glu Ala Cys Ile Arg Gly
                165                 170                 175 tat aat cct gga ctt ctg gtg cat tct gac ctt gcc tat cta caa gca        576
Tyr Asn Pro Gly Leu Leu Val His Ser Asp Leu Ala Tyr Leu Gln Ala
            180                 185                 190 gaa ggc gga gga gac cgg caa ctc aca gac aga gag aag gag atc atc        624
Glu Gly Gly Gly Asp Arg Gln Leu Thr Asp Arg Glu Lys Glu Ile Ile
        195                 200                 205 cgc cag gca gcc gtg cag cag acc aag gag atg gac ctg agc gtg gtg        672
Arg Gln Ala Ala Val Gln Gln Thr Lys Glu Met Asp Leu Ser Val Val
    210                 215                 220 cgc ctc atg ttc aca gcc ttc ctc cct gac agc act ggc agc ttc act        720
Arg Leu Met Phe Thr Ala Phe Leu Pro Asp Ser Thr Gly Ser Phe Thr
225                 230                 235                 240 cgg aga ctg gag cct gtg gtg tca gac gcc atc tat gat agc aaa gcc        768
Arg Arg Leu Glu Pro Val Val Ser Asp Ala Ile Tyr Asp Ser Lys Ala
                245                 250                 255 ccg aat gca tcc aac ctg aaa atc gtg aga atg gac aga aca gca gga        816
Pro Asn Ala Ser Asn Leu Lys Ile Val Arg Met Asp Arg Thr Ala Gly
            260                 265                 270 tgt gtg acg gga ggg gag gag att tac ctt ctc tgt gac aag gtt cag        864
Cys Val Thr Gly Gly Glu Glu Ile Tyr Leu Leu Cys Asp Lys Val Gln
        275                 280                 285 aaa gat gac atc cag att cgg ttt tat gaa gag gaa gaa aat ggc gga        912
```

```
                Lys Asp Asp Ile Gln Ile Arg Phe Tyr Glu Glu Glu Asn Gly Gly
                    290                 295                 300 gtt tgg gaa gga ttt ggg gac ttt tcc ccc acg gat gtt cat aga cag        960
Val Trp Glu Gly Phe Gly Asp Phe Ser Pro Thr Asp Val His Arg Gln
305                 310                 315                 320 ttt gcc att gtc ttc aaa acg cca aag tat aag gat gtc aac att aca       1008
Phe Ala Ile Val Phe Lys Thr Pro Lys Tyr Lys Asp Val Asn Ile Thr
                325                 330                 335 aag cca gct tcc gtg ttt gtt cag ctt cgg agg aaa tca gac ctg gaa       1056
Lys Pro Ala Ser Val Phe Val Gln Leu Arg Arg Lys Ser Asp Leu Glu
                340                 345                 350 act agt gaa ccg aaa ccc ttt ctc tac tac cct gaa atc aaa gac aaa       1104
Thr Ser Glu Pro Lys Pro Phe Leu Tyr Tyr Pro Glu Ile Lys Asp Lys
                355                 360                 365 gag gaa gtg caa agg aaa cgc cag aag ctg act agt aag gct ctg cag       1152
Glu Glu Val Gln Arg Lys Arg Gln Lys Leu Thr Ser Lys Ala Leu Gln
    370                 375                 380 ctc gcc agg cga cac gcc aac gcc ctt ttc gac tac gca gtg acg ggg       1200
Leu Ala Arg Arg His Ala Asn Ala Leu Phe Asp Tyr Ala Val Thr Gly
385                 390                 395                 400 gat gtg aag atg ttg ctg gcc gtg caa cgc cat ctc acc gcc gtg cag       1248
Asp Val Lys Met Leu Leu Ala Val Gln Arg His Leu Thr Ala Val Gln
                405                 410                 415 gat gag aat ggg gac agt gtc tta cac tta gcc atc atc cac ctc cac       1296
Asp Glu Asn Gly Asp Ser Val Leu His Leu Ala Ile Ile His Leu His
                420                 425                 430 gct cag ctc gtg agg gat ctg ctg gaa gtc aca tct ggt ttg atc tct       1344
Ala Gln Leu Val Arg Asp Leu Leu Glu Val Thr Ser Gly Leu Ile Ser
                435                 440                 445 gat gac atc atc aac atg aga aat gac ctg tat cag aca cct ctg cac       1392
Asp Asp Ile Ile Asn Met Arg Asn Asp Leu Tyr Gln Thr Pro Leu His
450                 455                 460 ttg gcc gtg atc acc aag cag gaa gat gta gta gag gat ttg ctg agg       1440
Leu Ala Val Ile Thr Lys Gln Glu Asp Val Val Glu Asp Leu Leu Arg
465                 470                 475                 480 gtt ggg gct gac ctg agc ctt ctg gac cgc tgg ggc aac tct gtc ctg       1488
Val Gly Ala Asp Leu Ser Leu Leu Asp Arg Trp Gly Asn Ser Val Leu
                485                 490                 495 cac cta gct gcc aaa gaa gga cac gac aga atc ctc agc atc ctg ctc       1536
His Leu Ala Ala Lys Glu Gly His Asp Arg Ile Leu Ser Ile Leu Leu
                500                 505                 510 aag agc aga aaa gca gcg ccc ctt atc gac cac ccc aat ggg gaa ggt       1584
Lys Ser Arg Lys Ala Ala Pro Leu Ile Asp His Pro Asn Gly Glu Gly
                515                 520                 525 cta aat gcc atc cac ata gct gtg atg agc aat agc ctg cca tgt ctg       1632
Leu Asn Ala Ile His Ile Ala Val Met Ser Asn Ser Leu Pro Cys Leu
530                 535                 540 ctg ctg ctg gtg gct gcc ggg gca gaa gtc aat gct cag gag cag aag       1680
Leu Leu Leu Val Ala Ala Gly Ala Glu Val Asn Ala Gln Glu Gln Lys
545                 550                 555                 560 tct ggg cgc acg ccg ctg cac ctg gcc gtg gag tac gac aac atc tcc       1728
Ser Gly Arg Thr Pro Leu His Leu Ala Val Glu Tyr Asp Asn Ile Ser
                565                 570                 575 ttg gct ggc tgc ctg ctt ctg gag ggt gat gcc cac gtg gac agt acc       1776
Leu Ala Gly Cys Leu Leu Leu Glu Gly Asp Ala His Val Asp Ser Thr
                580                 585                 590 acc tat gat ggg act aca cct ctg cat ata gcg gcc gga aga ggg tcc       1824
Thr Tyr Asp Gly Thr Thr Pro Leu His Ile Ala Ala Gly Arg Gly Ser
                595                 600                 605 acc aga ctg gca gct ctt ctc aaa gca gca gga gca gac ccc ctg gtg       1872
```

```
Thr Arg Leu Ala Ala Leu Leu Lys Ala Ala Gly Ala Asp Pro Leu Val
    610             615                 620 gag aac ttt gag cct ctc tat gac ctg gac gac tct tgg gag aag gct    1920
Glu Asn Phe Glu Pro Leu Tyr Asp Leu Asp Asp Ser Trp Glu Lys Ala
625                 630                 635                 640 gga gaa gat gag gga gtg gtg cca ggt acc aca ccc ctg gac atg gct    1968
Gly Glu Asp Glu Gly Val Val Pro Gly Thr Thr Pro Leu Asp Met Ala
                645                 650                 655 gcc aac tgg cag gta ttt gac ata cta aat ggg aaa ccg tat gag cct    2016
Ala Asn Trp Gln Val Phe Asp Ile Leu Asn Gly Lys Pro Tyr Glu Pro
            660                 665                 670 gtg ttc aca tct gat gat ata cta cca gga tcc tag                    2052
Val Phe Thr Ser Asp Asp Ile Leu Pro Gly Ser
        675                 680

<210> SEQ ID NO 8
<211> LENGTH: 683
<212> TYPE: PRT
<213> ORGANISM: Mus musculus

<400> SEQUENCE: 8

Met Ala Ser Met Thr Gly Gly Gln Gln Met Gly Thr Gly Ser Met Ala
1               5                   10                  15

Asp Asp Asp Pro Tyr Gly Thr Gly Gln Met Phe His Leu Asn Thr Ala
            20                  25                  30

Leu Thr His Ser Ile Phe Asn Ala Glu Leu Tyr Ser Pro Glu Ile Pro
        35                  40                  45

Leu Ser Thr Asp Gly Pro Tyr Leu Gln Ile Leu Glu Gln Pro Lys Gln
    50                  55                  60

Arg Gly Phe Arg Phe Arg Tyr Val Cys Glu Gly Pro Ser His Gly Gly
65                  70                  75                  80

Leu Pro Gly Ala Ser Ser Glu Lys Asn Lys Lys Ser Tyr Pro Gln Val
                85                  90                  95

Lys Ile Cys Asn Tyr Val Gly Pro Ala Lys Val Ile Val Gln Leu Val
            100                 105                 110

Thr Asn Gly Lys Asn Ile His Leu His Ala His Ser Leu Val Gly Lys
        115                 120                 125

His Cys Glu Asp Gly Val Cys Thr Val Thr Ala Gly Pro Lys Asp Met
    130                 135                 140

Val Val Gly Phe Ala Asn Leu Gly Ile Leu His Val Thr Lys Lys Lys
145                 150                 155                 160

Val Phe Glu Thr Leu Glu Ala Arg Met Thr Glu Ala Cys Ile Arg Gly
                165                 170                 175

Tyr Asn Pro Gly Leu Leu Val His Ser Asp Leu Ala Tyr Leu Gln Ala
            180                 185                 190

Glu Gly Gly Gly Asp Arg Gln Leu Thr Asp Arg Glu Lys Glu Ile Ile
        195                 200                 205

Arg Gln Ala Ala Val Gln Gln Thr Lys Glu Met Asp Leu Ser Val Val
    210                 215                 220

Arg Leu Met Phe Thr Ala Phe Leu Pro Asp Ser Thr Gly Ser Phe Thr
225                 230                 235                 240

Arg Arg Leu Glu Pro Val Val Ser Asp Ala Ile Tyr Asp Ser Lys Ala
                245                 250                 255

Pro Asn Ala Ser Asn Leu Lys Ile Val Arg Met Asp Arg Thr Ala Gly
            260                 265                 270

Cys Val Thr Gly Gly Glu Glu Ile Tyr Leu Leu Cys Asp Lys Val Gln
        275                 280                 285
```

Lys Asp Asp Ile Gln Ile Arg Phe Tyr Glu Glu Glu Asn Gly Gly
290 295 300

Val Trp Glu Gly Phe Gly Asp Phe Ser Pro Thr Asp Val His Arg Gln
305 310 315 320

Phe Ala Ile Val Phe Lys Thr Pro Lys Tyr Lys Asp Val Asn Ile Thr
325 330 335

Lys Pro Ala Ser Val Phe Val Gln Leu Arg Arg Lys Ser Asp Leu Glu
340 345 350

Thr Ser Glu Pro Lys Pro Phe Leu Tyr Tyr Pro Glu Ile Lys Asp Lys
355 360 365

Glu Glu Val Gln Arg Lys Arg Gln Lys Leu Thr Ser Lys Ala Leu Gln
370 375 380

Leu Ala Arg Arg His Ala Asn Ala Leu Phe Asp Tyr Ala Val Thr Gly
385 390 395 400

Asp Val Lys Met Leu Leu Ala Val Gln Arg His Leu Thr Ala Val Gln
405 410 415

Asp Glu Asn Gly Asp Ser Val Leu His Leu Ala Ile Ile His Leu His
420 425 430

Ala Gln Leu Val Arg Asp Leu Leu Glu Val Thr Ser Gly Leu Ile Ser
435 440 445

Asp Asp Ile Ile Asn Met Arg Asn Asp Leu Tyr Gln Thr Pro Leu His
450 455 460

Leu Ala Val Ile Thr Lys Gln Glu Asp Val Val Glu Asp Leu Leu Arg
465 470 475 480

Val Gly Ala Asp Leu Ser Leu Leu Asp Arg Trp Gly Asn Ser Val Leu
485 490 495

His Leu Ala Ala Lys Glu Gly His Asp Arg Ile Leu Ser Ile Leu Leu
500 505 510

Lys Ser Arg Lys Ala Ala Pro Leu Ile Asp His Pro Asn Gly Glu Gly
515 520 525

Leu Asn Ala Ile His Ile Ala Val Met Ser Asn Ser Leu Pro Cys Leu
530 535 540

Leu Leu Leu Val Ala Ala Gly Ala Glu Val Asn Ala Gln Glu Gln Lys
545 550 555 560

Ser Gly Arg Thr Pro Leu His Leu Ala Val Glu Tyr Asp Asn Ile Ser
565 570 575

Leu Ala Gly Cys Leu Leu Leu Glu Gly Asp Ala His Val Asp Ser Thr
580 585 590

Thr Tyr Asp Gly Thr Thr Pro Leu His Ile Ala Ala Gly Arg Gly Ser
595 600 605

Thr Arg Leu Ala Ala Leu Leu Lys Ala Ala Gly Ala Asp Pro Leu Val
610 615 620

Glu Asn Phe Glu Pro Leu Tyr Asp Leu Asp Asp Ser Trp Glu Lys Ala
625 630 635 640

Gly Glu Asp Glu Gly Val Val Pro Gly Thr Thr Pro Leu Asp Met Ala
645 650 655

Ala Asn Trp Gln Val Phe Asp Ile Leu Asn Gly Lys Pro Tyr Glu Pro
660 665 670

Val Phe Thr Ser Asp Asp Ile Leu Pro Gly Ser
675 680

<210> SEQ ID NO 9
<211> LENGTH: 21
<212> TYPE: DNA

```
<213> ORGANISM: Artificial Sequence
<220> FEATURE:
<223> OTHER INFORMATION: Description of Artificial Sequence: Primer

<400> SEQUENCE: 9
cgggatccat ggcagacgat g                                              21

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
cccaagcttt tcctctttgt ctttgatttc                                     30

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
gactagtaag gctctgcagc tcgcc                                          25

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 12
gctctagact aaattttgcc ttcaatagg                                      29

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
cgggatccat ggcagacgat g                                              21

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
ggaattcgga tcctggtagt atatcatcag                                     30
```